(12) United States Patent
Golberg et al.

(10) Patent No.: US 10,183,163 B2
(45) Date of Patent: Jan. 22, 2019

(54) SYSTEMS AND METHODS FOR DELIVERING PULSED ELECTRIC FIELDS TO SKIN TISSUE

(71) Applicant: THE GENERAL HOSPITAL CORPORATION, Boston, MA (US)

(72) Inventors: Alexander Golberg, Boston, MA (US); Martin L. Yarmush, Newton, MA (US); Robert L. Sheridan, Lexington, MA (US); William Gerald Austen, Weston, MA (US); G. Felix Broelsch, Boston, MA (US); Boris Rubinsky, El Cerrito, CA (US); Michael Belkin, Tel Aviv (IL)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 14/655,178

(22) PCT Filed: Dec. 26, 2013

(86) PCT No.: PCT/US2013/007829
§ 371 (c)(1),
(2) Date: Jun. 24, 2015

(87) PCT Pub. No.: WO2014/105964
PCT Pub. Date: Jul. 3, 2014

(65) Prior Publication Data
US 2016/0213922 A1    Jul. 28, 2016

Related U.S. Application Data

(60) Provisional application No. 61/746,191, filed on Dec. 27, 2012, provisional application No. 61/835,025, (Continued)

(51) Int. Cl.
*A61N 1/32* (2006.01)
*A61N 1/36* (2006.01)
(Continued)

(52) U.S. Cl.
CPC ....... *A61N 1/36014* (2013.01); *A61N 1/0464* (2013.01); *A61N 1/0468* (2013.01);
(Continued)

(58) Field of Classification Search
CPC .. A61N 1/0412; A61N 1/0464; A61N 1/0468; A61N 1/205; A61N 1/326;
(Continued)

(56) References Cited

U.S. PATENT DOCUMENTS

2003/0153960 A1* 8/2003 Chornenky .......... A61N 1/0502
607/72
2006/0269531 A1* 11/2006 Beebe .................. A61N 1/0412
424/93.21

(Continued)

OTHER PUBLICATIONS

Golberg et al. "In vivo non-thermal irreversible electroporation impact on rat liver galvanic apparent internal resistance." Phys Med Biol. Feb. 21, 2011;56(4):951-63. doi: 10.1088/0031-9155/56/4/005. Epub Jan. 20, 2011.*

(Continued)

*Primary Examiner* — Eugene T Wu
(74) *Attorney, Agent, or Firm* — Quarles & Brady LLP

(57) ABSTRACT

Systems and methods for controlling a tissue of a subject using applied pulsed electric fields. The system for controlling a therapy provided to a tissue of a subject using applied pulsed electric fields. The system includes an electrode assembly configured to engage a skin tissue of a subject to deliver a series of electric field pulses to the skin tissue and a user input configured to receive an operational instruction for the series of electric field pulses. The operational instruc-
(Continued)

tion defines at least one of a pulse duration, a pulse frequency, a pulse number, and a pulse amplitude. The system also includes at least one processor configured to access the operational instruction received by the user input and, using the operational instruction, create an electric field profile to be generated by the electrode assembly about the skin tissue of the subject to control a fibroblast characteristic while preserving a vascular perfusion in at least a portion of the skin tissue. The processor is also caused to control the electrode assembly using the electric field profile to deliver the series of electric field pulses to control the fibroblast characteristic.

7 Claims, 24 Drawing Sheets

Related U.S. Application Data filed on Jun. 14, 2013, provisional application No. 61/868,118, filed on Aug. 21, 2013.

(51) Int. Cl.
*A61N 1/04* (2006.01)
*A61B 18/00* (2006.01)

(52) U.S. Cl.
CPC ......... *A61N 1/0476* (2013.01); *A61N 1/0492* (2013.01); *A61N 1/326* (2013.01); *A61N 1/328* (2013.01); *A61B 2018/00613* (2013.01); *A61N 1/325* (2013.01); *A61N 1/327* (2013.01)

(58) Field of Classification Search
CPC ...... A61N 1/327; A61N 1/328; A61N 1/3615; A61N 1/36153; A61N 1/36157; A61N 1/3616; A61N 1/36167; A61N 1/36171; A61N 1/36175; A61N 1/36178; A61B 2018/00613
See application file for complete search history.

(56) References Cited

U.S. PATENT DOCUMENTS

| | | | | |
|---|---|---|---|---|
| 2010/0030211 A1* | 2/2010 | Davalos | .............. | A61N 1/327 606/41 |
| 2011/0092973 A1* | 4/2011 | Nuccitelli | .............. | A61N 1/205 606/49 |
| 2011/0118732 A1* | 5/2011 | Rubinsky | .............. | A61N 1/0412 606/41 |
| 2011/0137229 A1* | 6/2011 | Palti | .............. | A61N 1/32 604/20 |
| 2013/0253415 A1* | 9/2013 | Sano et al. | .............. | A61B 18/14 604/20 |

OTHER PUBLICATIONS

Golberg et al. "Intermittently Delivered Pulsed Electric Fields for Sterile Storage of Turbid Media." IEEE Transactions on Plasma Science, vol. 38, No. 11, pp. 3211-3218, Nov. 2010. doi: 10.1109/TPS.2010.2065246.*
Rubinsky et al. "Irreversible Electroporation". Series in Biomedical Engineering. Springer. 2010.*
S. J. Beebe, P. M. Fox, L. J. Rec, K. Somers, R. H. Stark and K. H. Schoenbach, "Nanosecond pulsed electric field (nsPEF) effects on cells and tissues: apoptosis induction and tumor growth inhibition," in IEEE Transactions on Plasma Science, vol. 30, No. 1, pp. 286-292, Feb. 2002. doi: 10.1109/TPS.2002.1003872.*
Davalos et al. "Tissue ablation with irreversible electroporation." Ann Biomed Eng. Feb. 2005;33(2):223-31.*
Nuccitelli et al. "Nanosecond pulsed electric fields cause melanomas to self-destruct." Biochem Biophys Res Commun. May 5, 2006; 343(2): 351-360. Published online Mar. 10, 2006. doi: 10.1016/j.bbrc.2006.02.181.*
Thomson et al. "Investigation of the safety of irreversible electroporation in humans."J Vasc Interv Radiol. May 2011;22(5):611-21. doi: 10.1016/j.jvir.2010.12.014. Epub Mar. 25, 2011.*
Pucihar et al. "Equivalent pulse parameters for electroporation."IEEE Trans Biomed Eng. Nov. 2011;58(11):3279-88. doi: 10.1109/TBME.2011.2167232. Epub Sep. 6, 2011.*
Golberg, A., Bei, M., Sheridan, R. L. and Yarmush, M. L. (2013), Regeneration and control of human fibroblast cell density by intermittently delivered pulsed electric fields. Biotechnol. Bioeng. . . . doi:10.1002/bit.24832.*
Golberg A, Broelsch GF, Bohr S, et al. Non-thermal, pulsed electric field cell ablation: A novel tool for regenerative medicine and scarless skin regeneration.Technology. 2013;1(1):1-8. doi:10.1142/S233954781320001X.*
Golberg A, Broelsch GF, Vecchio D, et al. Eradication of multidrug-resistant A. baumannii in burn wounds by antiseptic pulsed electric field. Technology. 2014;2(2):153-160.*
Golberg A, Broelsch GF, Vecchio D, et al. Pulsed Electric Fields for Burn Wound Disinfection in a Murine Model. Journal of burn care & research : official publication of the American Burn Association. 2015;36(1):7-13. doi:10.1097/BCR.0000000000000157.*
Golberg A, Khan S, Belov V, et al. Skin Rejuvenation with Non-Invasive Pulsed Electric Fields. Scientific Reports. 2015;5:10187. doi:10.1038/srep10187.*
Alexander Golberg, Martin Villiger, Saiqa Khan, Kyle P. Quinn, William C.Y. Lo, Brett E. Bouma, Martin C. Mihm Jr., William G. Austen Jr., Martin L. Yarmush, Preventing Scars after Injury with Partial Irreversible Electroporation, Journal of Investigative Dermatology, Available online Jul. 5, 2016, ISSN 0022-202X, http://dx.doi.org/10.1016/j.jid.201.*
Webpage: Publications. Laboratory of Environmental Bioengineering, The Porter School of Environmental Studies, Tel Aviv University. <http://www.tau.ac.il/~agolberg/publications.html> Accessed Sep. 15, 2016.*
Charpentier, et al., Irreversible Electroporation of the Pancreas in Swine: A Pilot Study, HPB, 2010, 12:348-351.
Maor, et al., The Effect of Irreversible Electroporation of Blood Vessels, Technology in Cancer Research and Treatment, 2007, 6(4):307-312.
Phillips, et al., Irreversible Electroporation on the Small Intestine, British Journal of Cancer, 2012, 106:490-495.
Rubinsky, et al., Irreversible Electroporation: A New Ablation Modality—Clinical Implications, Technology in Cancer Research and Treatment, 2007, 6(1):1-12.

* cited by examiner

SYSTEMS AND METHODS FOR DELIVERING PULSED ELECTRIC FIELDS TO SKIN TISSUE

CROSS-REFERENCE

This application represents the national stage entry of PCT International Application No. PCT/US2013/077829 filed Dec. 26, 2013, which claims priority to U.S. Ser. No. 61/746,191 filed Dec. 27, 2012 and U.S. Ser. No. 61/835,025 filed Jun. 14, 2013, and U.S. Ser. No. 61/868,118 filed Aug. 21, 2013, the disclosures of which are incorporated by reference here in their entirety for all purposes.

BACKGROUND

The present disclosure relates generally to systems and methods for delivering electric fields to tissue and, in particular, to systems and methods for controlling and regenerating skin.

Wound care costs the U.S. healthcare system more than $20 billion each year. Among others, fire and burn injuries represent 1% of total injuries at a cost of $7.5 billion for total treatment and rehabilitation each year. In 2010 United States, a fire injury occurred every 30 minutes leading to 3,120 deaths and 17,720 injuries. Despite efforts, scars remain a major clinical and economic problem in the rehabilitation of burned and other injured patients, leading to physical, aesthetic, functional, psychological, and social stresses. Various approaches have been attempted over the years to treat scars, such as surgical excision, intra-lesional steroid and interferon injection, cryotherapy, laser therapy, irradiation, mechanical compression dressing, silicone sheet applications, to name a few. However, most treatments for keloidal and hypertrophic scars have offered minimal likelihood of improvement, with a recent meta review showing no statistically significant difference among the treatment options.

Wound healing is a dynamic, chronic process that is often divided into 4 overlapping phases: hemostasis, inflammation, proliferation, and remodeling. During hemostasis, constriction of the damaged vessels and clot formation physically limit blood loss. In the inflammatory phase, leukocytes and then monocytes accumulate to combat infection in the wounded tissue. In this phase, multiple cytokines and growth factors are released to the wound area and contribute to the fibroblast migration, differentiation and activity. During the proliferative phase, fibroblasts deposit new extracellular matrix and collagen and differentiate into myo-fibroblasts. In the final remodeling phase, re-organization of the closed wound environment occurs until repair is completed. Fetal wounds typically heal rapidly, without formation of a scab and with reduced inflammatory and angiogenic responses, exhibiting major differences compared to adult wound profiles of extracellular matrix and signaling. Moreover, in adults, the formation of hypertrophic scars (HTS) depends on the depth of injury and individual response, while in children, HTS are formed even in superficial wounds, burns and donor areas.

This complex dynamic process may be described using the concept of wound healing trajectory (FIG. 1A), which illustrates time-dependent cumulative effects of these multiple processes that occur from injury though healing. According to the healing trajectory curve, normally-healed tissues are characterized by complete restoration of function and structure. Chronic wounds, however, are characterized by incomplete restoration of structure and function. In proliferative scarring the healing process does not stop as it should and the tissue fails to reach a normal cell density and a balance between collagen deposition and degradation. Additionally, such processes may be further complicated by intrusion of infective biological pathogens or agents, interfering with repair processes and making clinical treatment more difficult.

Several systemic and genomic studies have identified potential cellular and extracellular factors that mediate the formation of proliferative scar. Current data show that alterations in coagulation, inflammation, angiogenesis, fibroplasia, contraction, remodeling, and mechanical tension correlate with the formation of HTS. However, the exact mechanisms associated with hypertrophic scarring have not yet been identified, leading to treatment procedures that have had limited clinical success. Thus, many conventional HSTs therapies do not take into account these complex interactions associated with would healing, and usually focus on a single target. For example, research on transforming growth factor ß (TGF-ß) revealed that TGF-ß1 and TGF-ß2 appear to be implicated in cutaneous scarring, while TGF-ß3 reduces scarring. However, a TGF-based therapy proposed thereafter failed in Phase III trials.

Humoral mediators appear to play an important role in proliferative scarring by altering fibroblast metabolism. It has been shown that signaling, which affects fibroblast metabolism, is different for individuals who suffer from proliferative scarring compared to those who do not. The major role of fibroblasts in wound healing is to replace the fibrin-based provisional matrix established during the inflammatory phase of wound healing with collagen-rich granulation tissue. The behavior of fibroblasts in the wound is highly dynamic (FIG. 1B) and varies at each healing phase. Fibroblasts reach the wound during the second or third day after the injury. Four days after the injury, fibroblasts are usually the major cell type in the developing granulation tissue. The wound fibroblast number increases initially through migration from nearby non-injured tissue and then through cell proliferation. Fibroblast density in the wound reaches its maximum between 7 and 14 days after injury. When the anatomic function of the tissue is mostly restored, the maturing granulation tissue undergoes remodeling leading to reduction of fibroblast density by apoptosis. Interestingly, clinical observations showed that in patients with proliferative scarring the apoptosis inhibitor—bcl-2 proto-oncogene is elevated while the apoptosis effector-interleukin-converting enzyme is decreased. These findings suggested that the apoptosis mechanisms are altered in patients with proliferative scarring.

Clinical control of cell density has been usually achieved by chemical factors, which affect the cell cycle, preventing or inducing proliferation. Such agents, however, cannot be precisely targeted and affect multiple cell types. For example, Tamoxifen, a synthetic non-steroidal anti-estrogen, has been shown to have multiple side effects. Those side effects include altered RNA transcription, decreased cellular proliferation, delay or arrest of the cells in the G1 phase of the cell cycle, and interference with multiple growth factors such as TGF-b and insulin-like growth factor.

In addition to efforts for improving wound care, the desire for a rejuvenated appearance has led to over 2.1 million skin rejuvenation procedures and accounted for 1.8 billion in spending in the US alone (2012) in the treatment of scars, striae, age-related rhytids, photodamage, acne, and trauma. In fact, minimally invasive aesthetic body shaping is the fastest growing sector of the rapidly expanding aesthetic market. From 1997 to 2012, there was a 500 percent increase in the total number of minimally-invasive procedures including skin resurfacing and laser procedures. This growth is driven by an aging population and increased social acceptance of aesthetic procedures, as well as significant emotional and psychological sequelae as result in physical alterations.

Overall, skin rejuvenation methods aim to remove damaged tissue and stimulate new growth of healthy collagen, skin cells, and elastin fibers. Currently the most popular therapies include percutaneous collagen induction (PCI) and laser therapies. PCI has a low side effect profile, but has very limited clinical data. Although laser treatments have good clinical data, they also have a poor side effect profile with many patients experiencing prolonged erythema, scaring, and dyspigmentation. The market needs a technology with fewer side effects, a better safety profile, lower cost, and one that is convenient enough to be sold over the counter.

Experimental data has shown that pulsed electric fields applied to cells may trigger multiple biochemical mechanisms, shown in FIG. 2, such as stimulating electric fields (SEF), reversible electroporation (RE), non-thermal irreversible electroporation (IRE), and thermal damages. These are known to affect cell and tissue metabolism by regenerative stimulation at the lower amplitudes, and, in addition, permeabilization at the higher ones. In the case of electroporation, the pulsed electric fields cause changes in cell membrane permeability, which may be reversible when the change in permeabilization is temporary, and cells survive. Applications of RE have involved gene delivery to cells and tissues, and cell fusion. In addition, RE has also been the basis for a new cancer treatment therapy, known as "electrochemotherapy," whereby cancer cell-specific cytotoxic drugs are introduced into cells through temporary membrane openings created by the pulsed electric fields.

Therefore, given the above, there is a need for systems and methods for controlling tissue and tissue regenerating processes using applied pulsed electric fields.

SUMMARY

The present invention overcomes the aforementioned drawbacks by providing systems and methods for delivering electric fields in a manner that controls or promotes tissue repair, enhancement, and disinfection. In particular, systems and methods provided may use non-thermal pulsed electric fields delivered periodically or intermittently to control a scar formation process or tissue enhancement process by way of selectively targeting specific cells types, or structures associated with immune system activation of repair or renewal pathways, without deleterious effects to desired tissue components, properties or processes, or non-target agents. In addition, systems and methods are provided that make use of antiseptic qualities of pulsed electric fields, providing for control of biological pathogens present in injured tissues or other infected sites.

In accordance with one aspect of the disclosure, a system for controlling a therapy provided to a tissue of a subject using applied pulsed electric fields is provided. The system includes an electrode assembly configured to engage a skin tissue of a subject to deliver a series of electric field pulses to the skin tissue and a user input configured to receive an operational instruction for the series of electric field pulses, the operational instruction defining at least one of a pulse duration, a pulse frequency, a pulse number, and a pulse amplitude. The system also includes at least one processor configured to access the operational instruction received by the user input and using the operational instruction, create an electric field profile to be generated by the electrode assembly about the skin tissue of the subject to control a fibroblast characteristic while preserving at least one of a vascular perfusion, an epithelium and an extracellular matrix in at least a portion of the skin tissue. The at least one processor is further configured to control the electrode assembly using the electric field profile to deliver the series of electric field pulses to control the fibroblast characteristic.

In accordance with another aspect of the disclosure, a method is provided for controlling a therapy delivered to a tissue of a subject using applied pulsed electric fields. The method includes receiving an operational instruction for a series of electric field pulses to be generated by an electrode assembly configured to engage a skin tissue of a subject to deliver the series of electric field pulses to the skin tissue, wherein the operational instruction defines at least one of a pulse duration, a pulse frequency, a pulse number, and a pulse amplitude. The method also includes creating, using the operational instruction, an electric field profile to be generated by the electrode assembly about the skin tissue of the subject to control a fibroblast characteristic while preserving at least one of a vascular perfusion, an epithelium and an extracellular matrix in at least a portion of the skin tissue. The method further includes controlling the electrode assembly using the electric field profile to deliver the series of electric field pulses to control the fibroblast characteristic and generating a report indicative of a spatiotemporal control of the fibroblast characteristic within the skin tissue of the subject.

In accordance with one aspect of the disclosure, a system for controlling a therapy provided to tissue of a subject using applied pulsed electric fields is provided. The system includes an electrode assembly configured to engage a wounded skin tissue of a subject to deliver a series of electric field pulses to the wounded skin tissue and a user input configured to receive an operational instruction for the series of electric field pulses, the operational instruction defining at least one of a pulse duration, a pulse frequency, a pulse number, and a pulse amplitude. The system also includes at least one processor configured to access the operational instruction received by the user input and using the operational instruction, create an electric field profile to be generated by the electrode assembly about the wounded skin tissue of the subject to control a biological pathogen concentration while preserving at least one of a vascular perfusion, an epithelium and an extracellular matrix in at least a portion of the wounded skin tissue. The at least one processor is further configured to control the electrode assembly using the electric field profile to deliver the series of electric field pulses to control the biological pathogen concentration.

The foregoing and other advantages of the invention will appear from the following description.

DETAILED DESCRIPTION

Figure 1B:
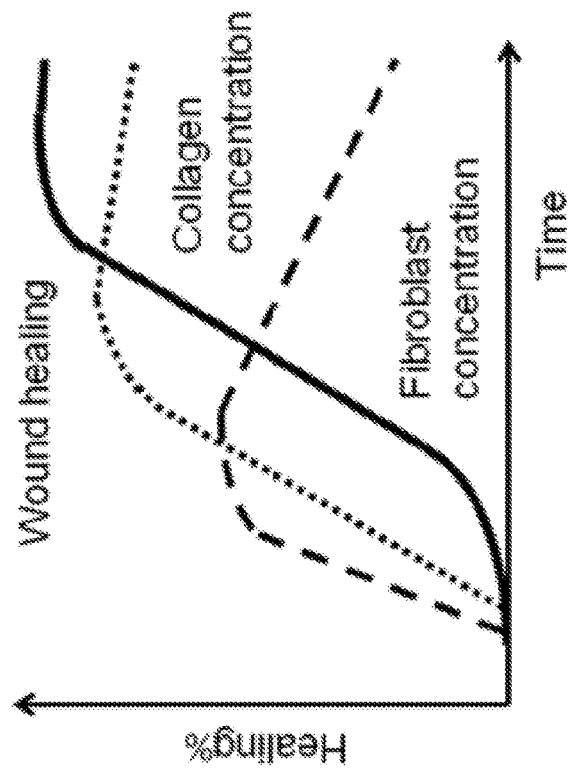
FIG. 1B is a scheme of fibroblast cell density dynamics during would repair.
Figure 1A:
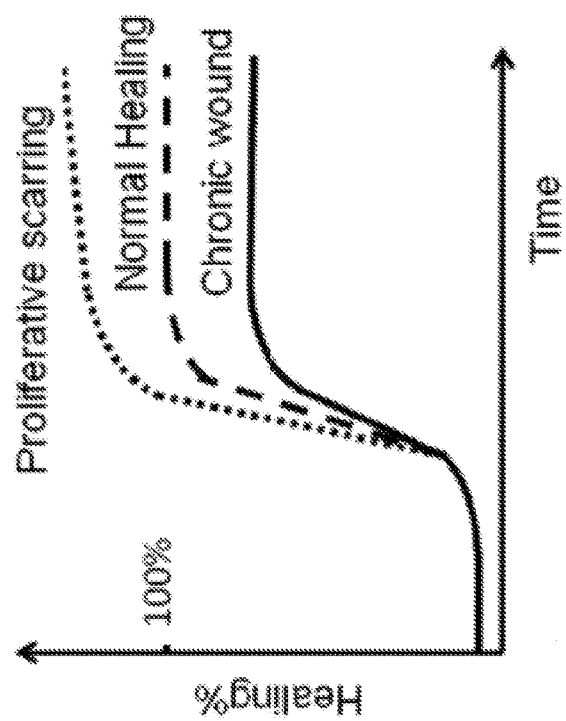
FIG. 1A is a graphical illustration of an exemplary wound healing trajectory.
Figure 2:
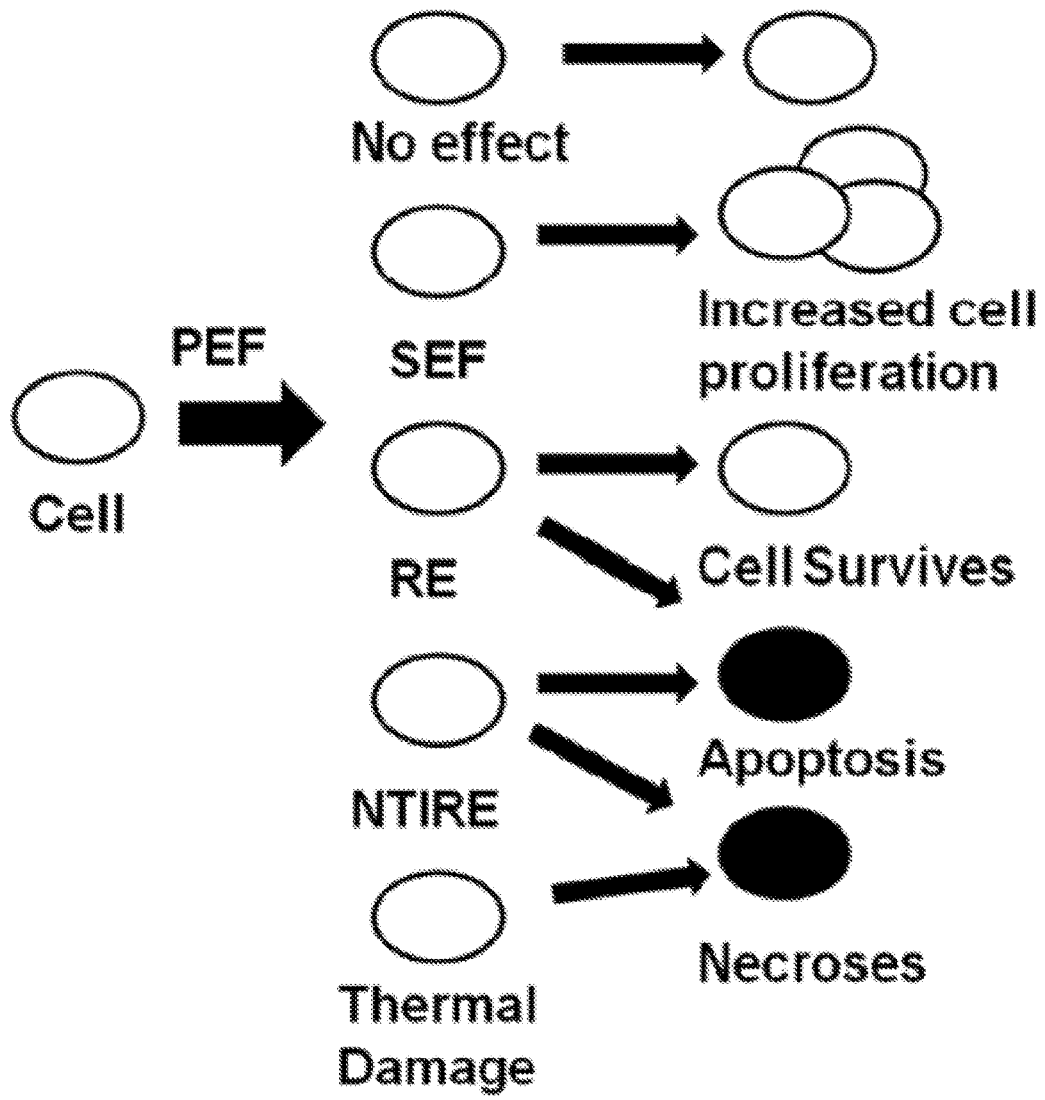
FIG. 2 is a schematic illustrating biochemical phenomena in cells induced by pulsed electric fields
Figure 3:
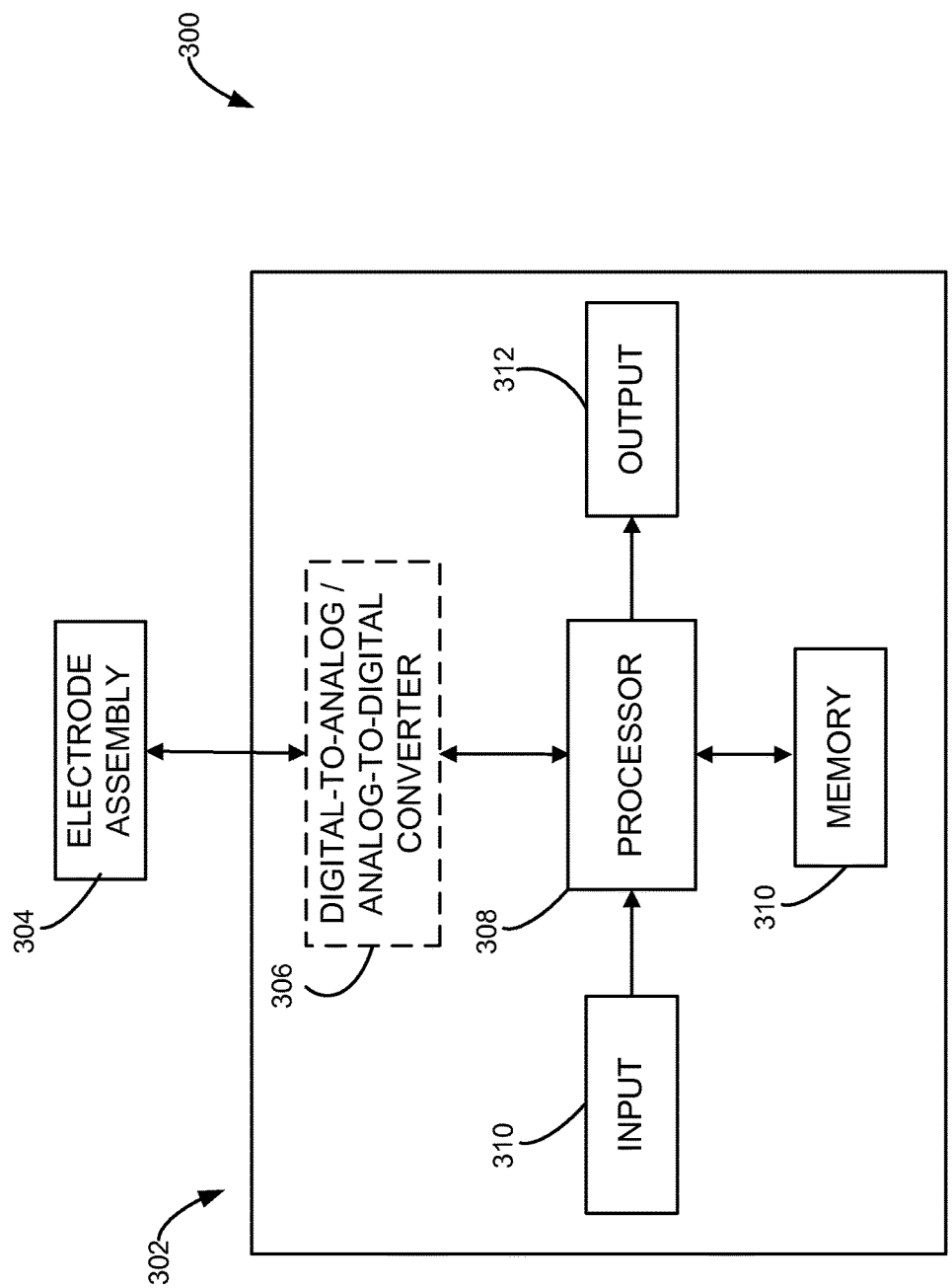
FIG. 3 is a schematic diagram of an illustrative system for use in accordance with the present invention.

FIG. 3 depicts a plan view of an illustrative system 300, which may be mobile, portable, or part of any system, device, apparatus or machine, for use in accordance with the present invention. The system 300 may be any device or apparatus capable of autonomously or semi-autonomously delivery of periodic or intermittent electric field pulses to tissues of a subject, such as skin. In this regard, system 300 may integrate a variety of software and hardware capabilities and functionality. As will be described, system 300 may be advantageously used in any setting intended for controlling a therapy designed to promote tissue repair or regenerating processes, as performed, for example, in a clinical practice addressed towards injuries or wounds, or cosmetic procedures, such as skin rejuvenation or enhancement.

The system 300 generally includes a controller 302, configured to generate, transmit and receive electronic signals from an electrode assembly 304 generally contacting a subject, and may also include a multi-channel converter 306 configured to convert digital to analog and analog to digital signals. An operational instruction defining the electric field pulses delivered by the controller 302 to the subject via the electrode assembly 304 may be provided by an operator or clinician, using any number of controllable input parameters, that may include pulse duration, pulse frequency, pulse number, pulse amplitude. Typical ranges of numerical values describing the electric field pulses may include 100 nanoseconds to 100 millisecond for the pulse durations, 0.1 to 5000 Hertz for the pulse frequencies, 1 to 5000 for the pulse numbers, and 10 to 5000 Volts for the pulse amplitudes, although other values may be possible. In some aspects, certain combinations of electric field pulse properties, as described, may be desirable to help minimize thermal effects to the tissues of a subject during operation of system 300. For example, such treatment configurations may be advantageous for generating non-thermal effects to the tissue of the subject, allowing for temperature increases of the tissues up to 40° C.

Additionally, certain designs of system 300 may include programmable and/or selectable settings on the controller 302 that may automatically generate pre-set combinations of the above-mentioned electric field pulse properties. Specifically, any such controllable input parameter combinations may be determined or selected with particular reference to controlling any number of desired biological targets, which may include certain cell types, constituents of cells or tissues, or any other agents found in or about skin tissue. For example, such targets for control may include a fibroblast cell density, immune cell density, collagen concentration or ellastin concentration, or any biological materials or pathogen concentration. In some aspects, operation of system 300 with specific combinations, as described, may preserve, reduce or enhance certain physiological functionalities, processes or mechanisms of the treated tissues. Such altered physiological functionalities, processes or mechanisms may be desirable in certain situations, such as wound repair or scar formation process, or an antiseptic process, as a result of a wound, injury or burn. For example, controlling a fibroblast cell density while retaining vascular perfusion, epithelium and extracellular matrix may reduce fibrosis, which is the formation of excess fibrous connective tissue in an organ or tissue during a reparative or reactive process. In addition, inducing or controlling a collagen or ellastin concentration may enhance the appearance of skin tissue in a skin renewal or rejuvenation process.

Figure 4:
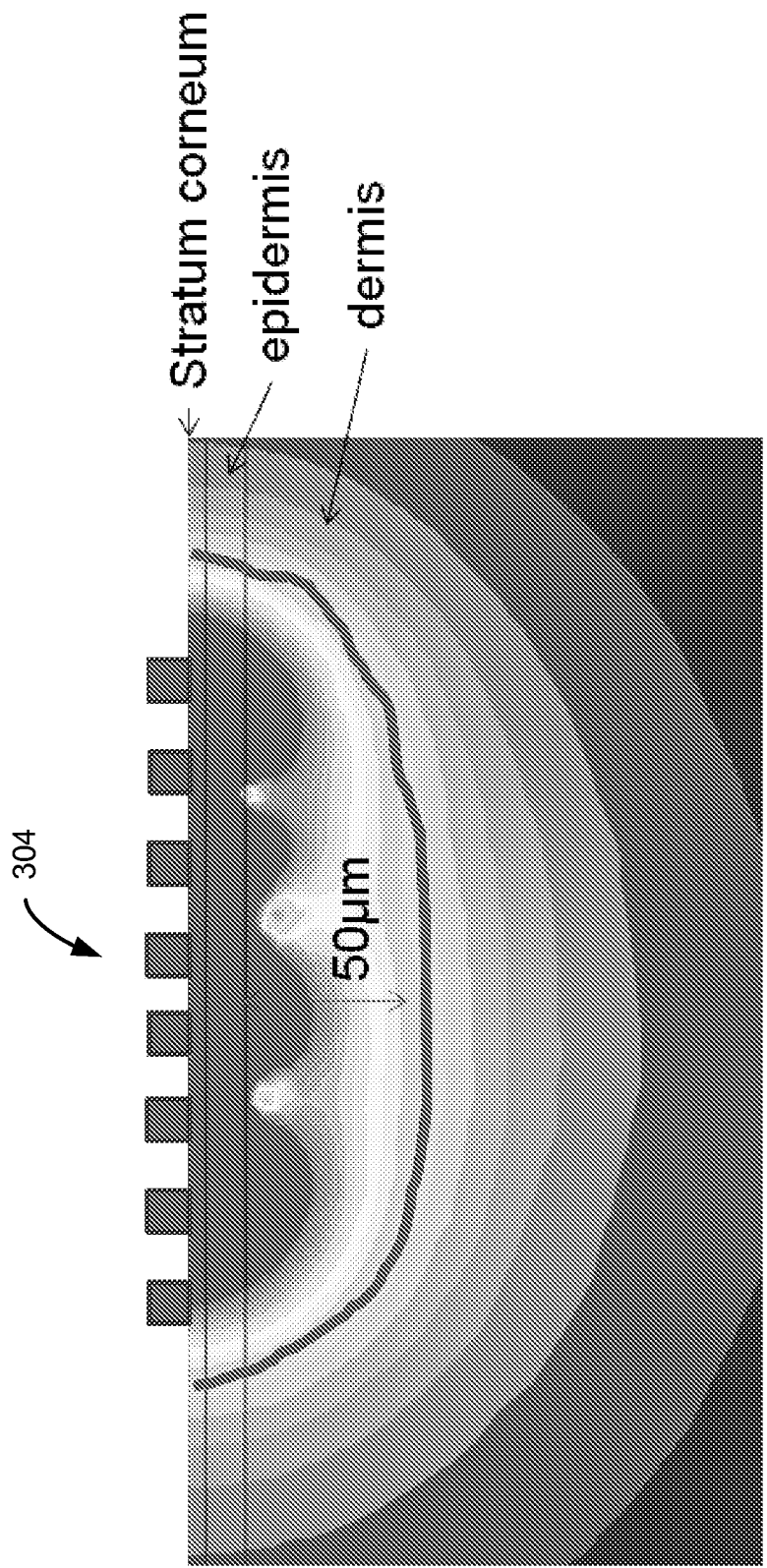
FIG. 4 is a schematic diagram illustrating an example electric field distribution in skin treated by pulsed electric fields, in accordance with the present invention.

The electrode assembly 304 may include a number of electrodes arranged in any specific geometry or spatial density, wherein individual electrodes may be designed to have any shapes, size, and geometrical separation, as necessary. The electrode assembly 304 may be removable with respect to system 300, or disposable, allowing for a range of flexibility and applications. In some aspects, the electrode assembly 304 may be designed to provide a sufficiently large skin area coverage as required by the specific application or procedure employing system 300. The electrode assembly 304 may also be designed to contact or adhere to skin surface of a subject via mechanical or chemically adhesive means. For example, the electrode assembly 304 may engage and be used to treat a wounded skin and any portion of surrounding healthy tissue. In some aspects, configurations related to electrode shape, size, and spatial density may be designed such that a desired electric field profile is achieved, which may preferably allow for a large tissue area coverage or a homogeneous distribution. For example, the electric field profile may be described by at least a voltage gradient, in a range between 10 and 5000 volts per millimeter, although other values are possible. FIG. 4 shows a schematic illustrating a computation model of an electric field distribution generated by an example electrode assembly 304. The electrode assembly 304 consists of 8 electrodes arranged on the skin tissue of a subject and energized by 24 Volts input, showing a spatial fall-off in electric field intensity away from the skin surface.

Additionally, the system 300 may be also equipped with sensors or capabilities (not shown in FIG. 3) for measuring any property or property signature, such as tissue temperature, conductivity or electric field permeability, or the presence of any biological agent or bacteria. Such sensors may be separate or integrated with the electrode assembly 304, and may be configured to detect, for example, a temperature profile of tissue proximate to the electrode assembly 304, providing information that may factor into the delivery of non-thermal electric field pulses, as described above.

Regardless of the particular hardware or software capabilities of the controller 302, the controller 302 shown in FIG. 3 may include some common hardware. For example, as described, the controller 302 may be configured to receive instruction from an operator regarding treatment parameters via a user input 310, for example, using buttons, touch displays, and the like. The controller 302 includes at least one processor 308 that is designed to carry out any number of actions. As will be described, the processor 308, in addition to other processing tasks, is capable of carrying out instructions for periodic and/or intermittent delivery of a sequence of electric field pulses. For example, the at least one processor 308 may be configured to deliver multiple pulsed electric field treatments for achieving a long term control of a fibroblast characteristic, collagen concentration, ellastin concentration, or a pathogen concentration, or any other target subject to pulsed electric field treatment. In some aspects, the at least one processor 308 may also be configured to carry out simulations or calculations of spatiotemporal profiles using stored or generated measurements of tissue properties, as described, and may provide feedback information in relation to delivery of electric field pulses.

The system 300 is also configured with a memory 310 is that may store instructions for operating the at least one processor 308. In addition, the memory 310 may be used by the processor for storing and retrieving raw and processed data. The controller 302 also includes an output 312, which may provide visual and/or audio indications to an operator. In some envisioned designs, the indications may alert the operator of a procedure condition, such as a temperature profile, task interruption or completion, or the presence or absence of a biological material. Of course a wide variety of additional hardware and software may be integrated with controller 302 to be controlled by or to communicate with the processor 308 such that, as will be described, the capabilities of the system 300 may be utilized for controlling tissue and regenerating processes using electric field pulses.

Figure 5:
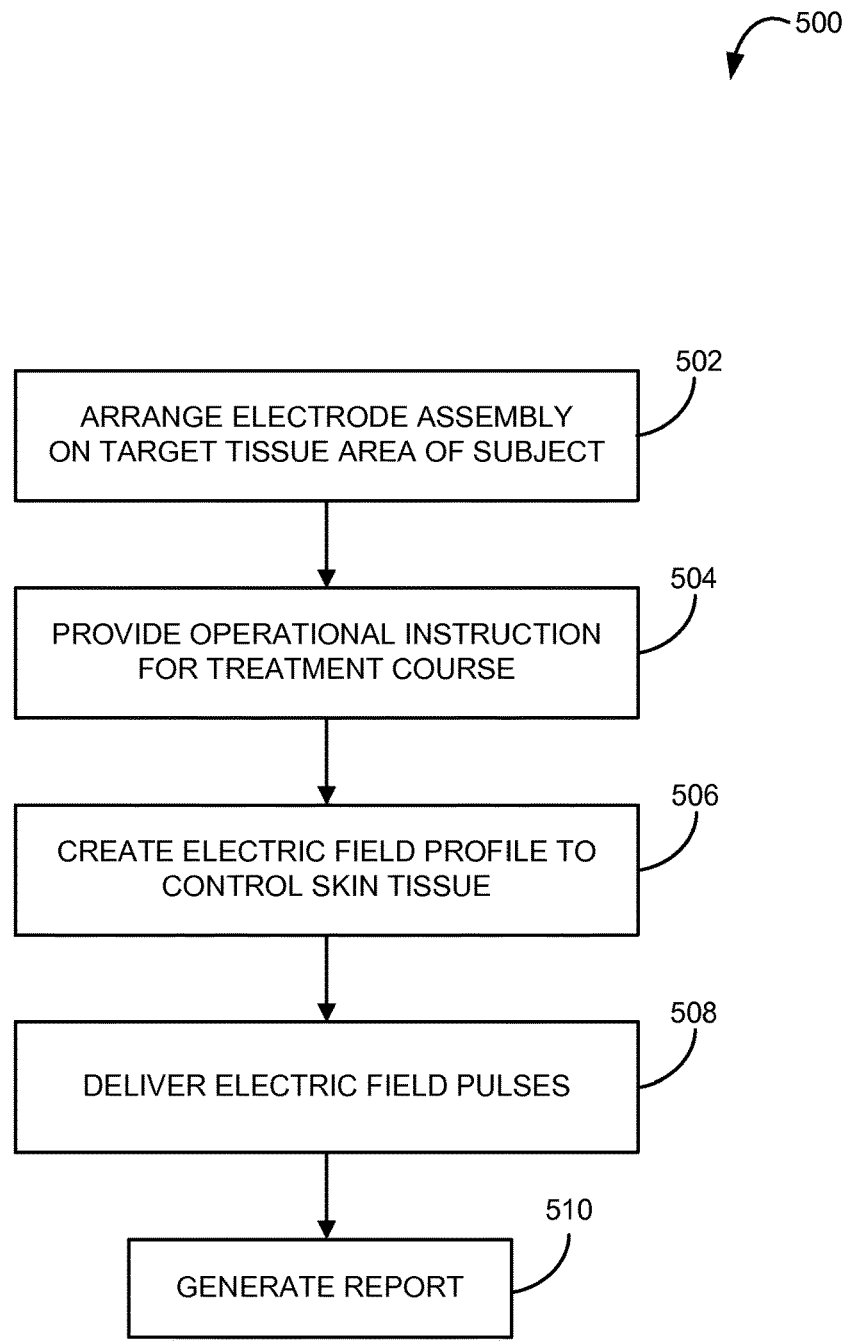
FIG. 5 is a flowchart illustrating the steps associated with a mode of operation of a system, in accordance with the present invention.

Referring to FIG. 5, exemplary steps of a process 500 for operation of system 300 in controlling tissue and regenerating processes are provided. Such method may be applied periodically or intermittently, as desired or necessary to control a target tissue, with the appropriate modification. The process 500 begins at process block 502 with arranging the electrode assembly onto or proximate to a targeted tissue location of a subject. At process block 504 an operator or clinician provides an operational instruction consistent with a desired treatment course or procedure. As described, the operational instruction may allow for adjustment of electric field pulse parameters, including pulse duration, pulse frequency, pulse number, pulse amplitude. In addition, other factors including voltages, currents, gradients, power factors, temperature and so on, delivered to the target tissue may also be taken into consideration with respect to the operational instruction. At process block 506 the operation instruction may be used to generate an electric field profile, as described, about the target tissue of the subject to control any desired biological materials. Then, at process block 508 the target tissue area is then treated with electric field pulses in accordance with selected or determined electric field pulse parameters by controlling the electrode assembly using the electric field profile. Then, at process block 510, a report is generated that may take any desired shape or form, including visual and/or audio indications to an operator or clinician. For example, such report may provide an indication of a spatiotemporal control of at least one biological material within the skin tissue of the subject, including a fibroblast characteristic, such as a cell density, function and metabolism, as well as a mast cell density, or any other immune cell density, epithelium, collagen concentration or ellastin concentration, or biological pathogen concentration.

The above-described systems and methods may be further understood by way of examples. These examples are offered for illustrative purposes only, and are not intended to limit the scope of the present invention in any way. Indeed, various modifications of the invention in addition to those shown and described herein will become apparent to those skilled in the art from the foregoing description and the following examples and fall within the scope of the appended claims. For example, certain electrode assemblies and configurations are presented, although it may be understood that other arrangements and geometries may be possible, and still considered to be well within the scope of the present invention. Likewise, specific process parameters and methods are recited that may be altered or varied based specific targets using variables such as pulse duration, pulse frequency, pulse number, pulse amplitude, as well as temporal profiles, intensities, voltages, power factors, currents, gradients, and so forth.

Example I

Figure 6:
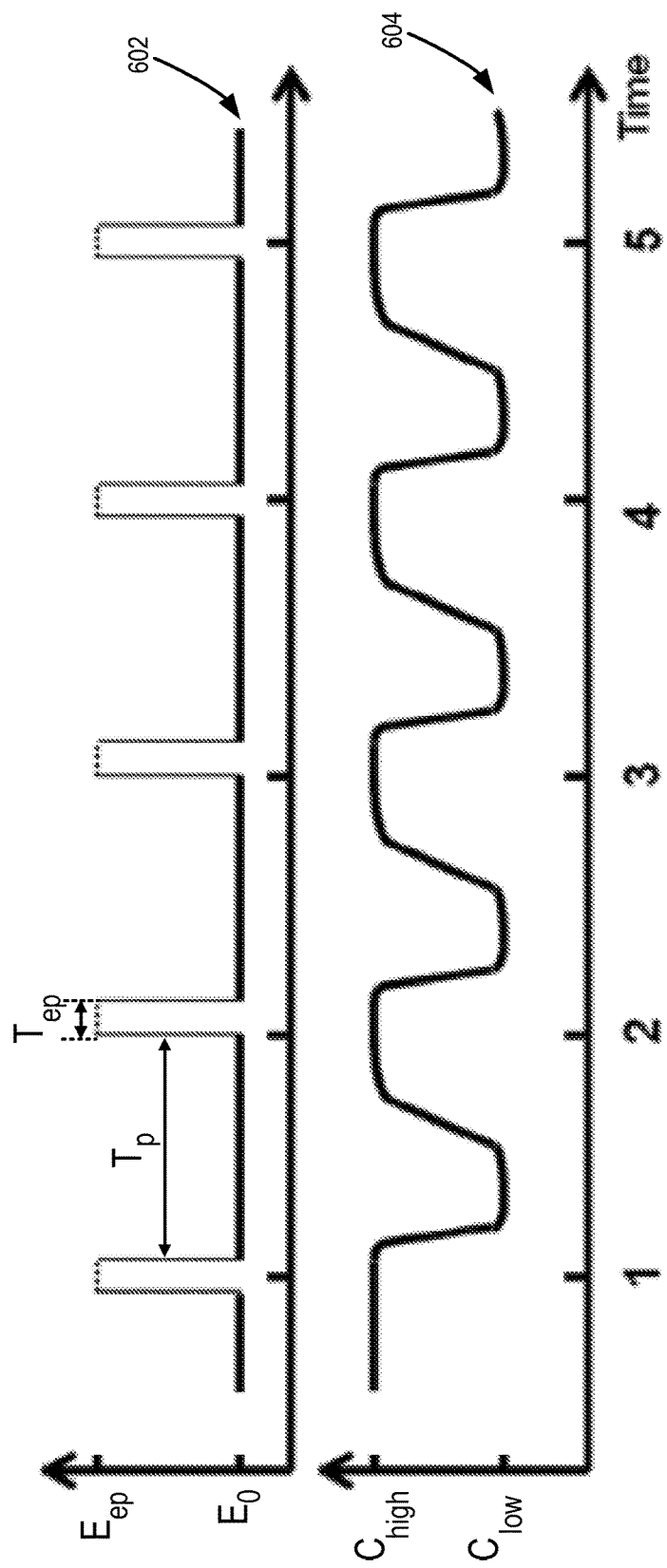
FIG. 6 is a schematic illustrating the effects of intermittently delivered pulsed electric fields on cell density concentration.

Previous modeling of non-thermal irreversible electroporation cell ablation in cancer has shown that only a fraction of cells exposed to specific pulsed electric field is killed, and surviving cells remain functional with the ability to regenerate. Also, experimental work on bacteria has demonstrated that intermittently delivered pulsed electric fields (IDPEF) can control microbial loads in perishable food products exposed to post processing contamination. For example, FIG. 6 shows the schematic of cell density control using IDPEF. The upper panel 602 in FIG. 6 describes the frequency and intensity of the applied electric fields over time, while the lower panel 604 describes cell density response to the applied treatment over time. The different parameters of FIG. 6 are described in Table I.

TABLE I

Parameters import for planning of IDPEF cell density control NHDF cell culture.

| Parameters | Units | Physical meaning |
|---|---|---|
| $E_o$ | Field intensity-E (V mm$^{-1}$), number of pulses- N pulse duration-t (s) frequency - f (Hz) | Electric field in applied on the cells population between the treatments |
| $E_{ep}$ | | Pulsed electric field applied on cell population during the treatment. |
| $T_p$ | s | Time interval between the treatment |
| $T_{ep}$ | s | Total time of the applied pulsed electric fields |
| $C_{high}$ | Cells ml$^{-1}$ or (%) | Higher threshold cell density/confluence % |
| $C_{low}$ | Cells ml$^{-1}$ or (%) | Lower threshold for cell density/confluence % |

Proliferative scarring is a human disease with neither available effective treatment nor relevant animal model. One hypothesis for scar formation involves deregulation of fibroblast signaling and delayed apoptosis. In this work, the response of normal human dermal fibroblast cultures (NDHF) to single and intermittently delivered pulsed electric field exposure was systematically investigated. A protocol developed for controlling NDHF cell density control using IDPEF involved doses and intervals to precisely control residual fibroblast density. In light of data showing that delayed fibroblast apoptosis may lead to proliferative scarring, results herein suggest a new method for fibroblast population control that may provide a potential treatment for this common and difficult clinical problem.

Materials and Methods
Cell Culture

All experiments were performed using third, fourth and fifth passage NHDF (ATCC, PCS-201-012). NHDF were cultured in Dulbecco's Modified Eagle Medium (DMEM) with 10% fetal bovine serum (FBS) (Life Technologies, Carlsbad, Calif.), at 37 C in a 5% $CO_2$ balance air atmosphere. The cells were cultured on 6 mm nominal diameter tissue culture treated dishes (Coring, Inc, NY). Immediately after the pulsed electric field treatment, cells were washed 3 times with phosphate-buffered saline (PBS), and then fresh DMEM/FBS was added. We changed the medium 2 hours after the treatment and every 24 hours subsequently.

Pulsed Electric Fields Dose Response

Electric field parameters are critical for electropermeabilisation, including field strength, E (V/mm), number of pulses, N, pulse duration, $T_{ep}$ (µs), and frequency, f (Hz). It was recently shown that specific changes in pulse amplitude, number and duration could lead to similar electroporation outcomes. For example, longer pulses or higher number of pulses, lower amplitudes are needed for the same fraction of electroporated cells. Therefore, to investigate the recovery time of the NHDF confluent cell culture after a single pulsed electric field treatment, the impact of N was tested. The other parameters of the protocol: E (V mm-1), t (s) and f (Hz), were fixed to the parameters close to those currently used in clinical settings. For partial ablation of the NHDF culture, pulsed electric fields were delivered directly to 6-well cell culture plate, using a BTX ECM 830 square-wave electroporator and a PetriPulser™ electrode (Harvard Apparatus Inc, MA).

Pulsed electric field parameters used in the present culture response study appear in Table II. We investigated the NHDF culture recovery after single pulsed electric fields treatment by live cell counting and cell culture recovery microscopic observations as described in the following sections.

TABLE II

Pulsed electric field parameters used in the present study.

| Parameters | Units | Used experimental values |
|---|---|---|
| E | V mm$^{-1}$ | 150 |
| $T_{ep}$ | µs | 70 |
| f | Hz | 1 |
| N | | 5, 10, 25, 50, 100 |

Intermittently Delivered Pulsed Electric Field Protocol

To demonstrate the control of NHDF cell density by IDPEF, pulsed electric fields were applied to cause ~60% cell death. The full recovery time of the surviving cells was 72 hours, as found from the experiments described in the previous section. Ten pulses with E (150 V/mm), t (70 µs) at 1 Hz were applied every 72 hours. The IDPEF protocol used appears in Table III. Culture recovery was assessed by live cell counting and microscopic observations as described in the following sections. Florescent imaging was not used in this study because of possible leakage of the florescent markers after cell exposure to strong electric fields.

TABLE III

IDPEF protocol for NHDF cell density control.

| Parameters | Values | Comments |
|---|---|---|
| $E_0$ | 0 | No electric field was applied between the treatments |
| $E_{ep}$ | E (150 V mm$^{-1}$) t (70 µs) f (1 Hz) N (10) | Pulsed electric field applied on cell population during the treatment. |
| $T_p$ | 72 (h) | Time interval between the treatment |
| $T_{ep}$ | 10 (s) | Total time of the delivery of pulsed electric fields |
| $C_{high}$ | 100% | Confluence of the 6 well plate |
| $C_{low}$ | 40% | Confluence of the 6 well plate |

Live Cell Counting

Two hours after pulsed electric fields treatment, cultured cells were detached from the plate by incubation with 1 mL of 0.25% trypsin and 0.02% EDTA for 10 min at 37 C (Life Technologies, Carlsbad, Calif.). The trypsin was inactivated by adding of 1 ml of DMEM/FBS media. Next, the cells were centrifuged at 800 rpm for 5 min (Allegra™6R Centrifuge, Beckman Coulter Inc). The cell pellet was re-suspended in PBS and an aliquot (10 ml) was removed for counting by hemocytometer (Hausser Scientific, USA).

Cell Culture Regeneration Imaging

The treated NHDF cultures were maintained in the same 6 well plates from the beginning till the end of the experiment. To monitor culture recovery the wells were observed by phase microscopy (Zeiss Axiovert 200M, Carl Zeiss MicroImaging, Inc.) Every 24 hours, 3 points in each well were captured at 2.5× magnification. Cell confluence at all three positions in the well defined the full recovery time point.

Statistical Analyses.

At least three replicates were used for each experimental condition, which were repeated at least three times. For statistical analyses, the Microsoft Office Excel 2010 external package was used.

Results

Human Dermal Fibroblast Dose Response to the Pulsed Electric Fields

Figure 7:
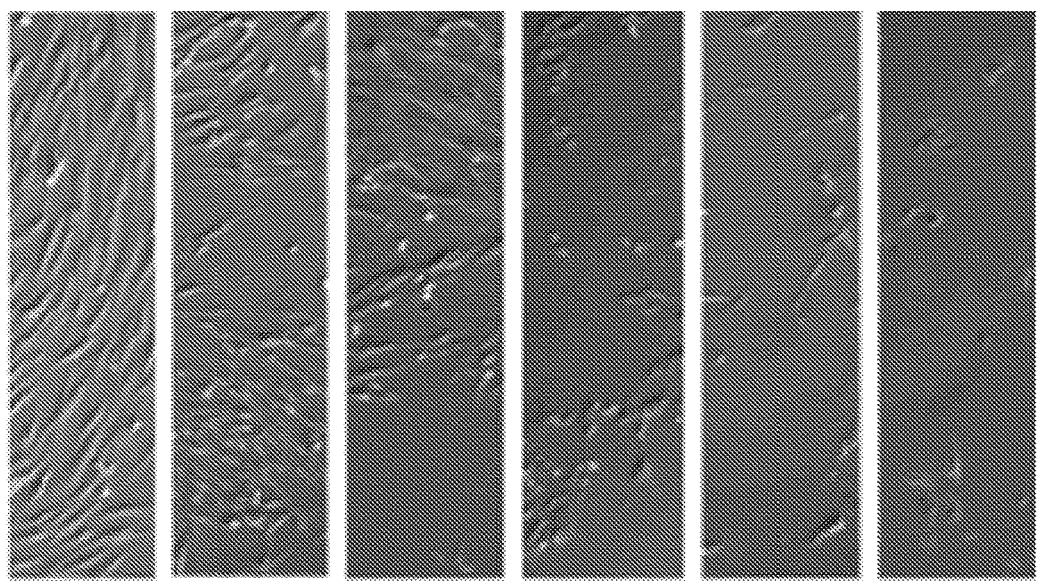
FIG. 7 is a graphical illustration representing the normal human dermal fibroblasts (NHDF) survival as a function of the number of electric field pulses.
Figure 7:
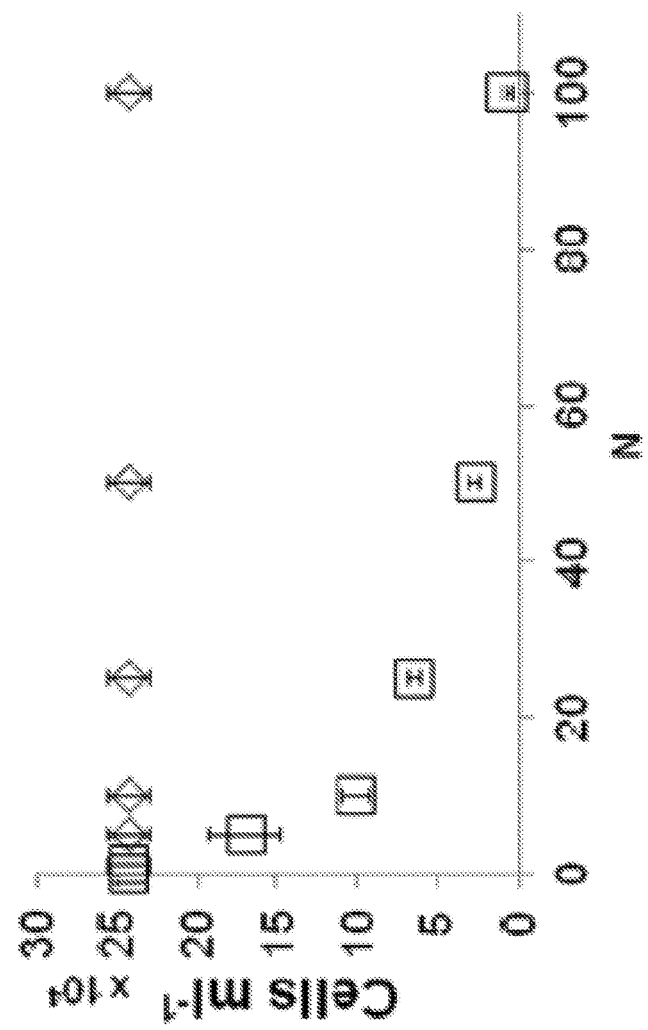

The survival of cells as a function of various number of electric field pulses subjected, as described in Table II, is illustrated in FIG. 7. The number of surviving cells were measured two hours after treatment to wash out any injured cells that may not have detached immediately. The graph illustrates a decrease in the surviving cells (square labels) versus N. The error bars indicated one standard deviation. In addition, FIG. 7 also shows the characteristic images of tissue dishes 2 hours after the treatment, with outcomes summarized in Table IV.

TABLE III

Cell survival after different number of electric field pulses.

| Number of Pulses (N) | Survivals (Cell ml$^{-1}$) × 10$^4$ |
|---|---|
| 0 (control) | 24.33 ± 1.28 |
| 5 | 17.06 ± 2.20 |
| 10 | 10.13 ± 0.80 |
| 25 | 6.46 ± 0.30 |
| 50 | 2.73 ± 0.41 |
| 100 | 0.73 ± 0.23 |

Figure 8A:
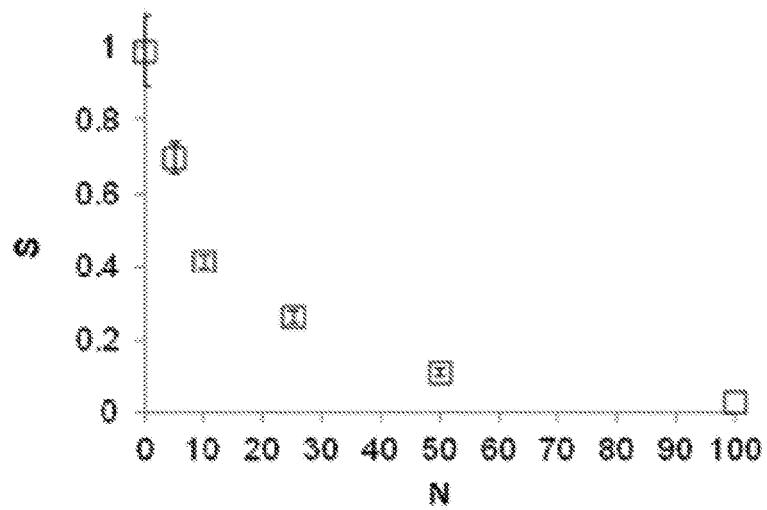
FIG. 8A is a graphical illustration representing the impact of number of pulses on the survival rate of NHDF.
Figure 8B:
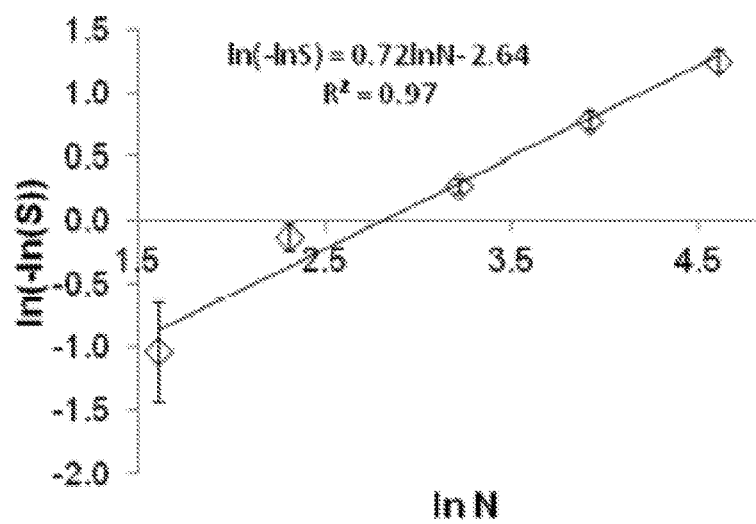
FIG. 8B is a graphical illustration representing the transformation of the survival function to linear form for estimation of Weibull distribution coefficients.
Figure 8C:
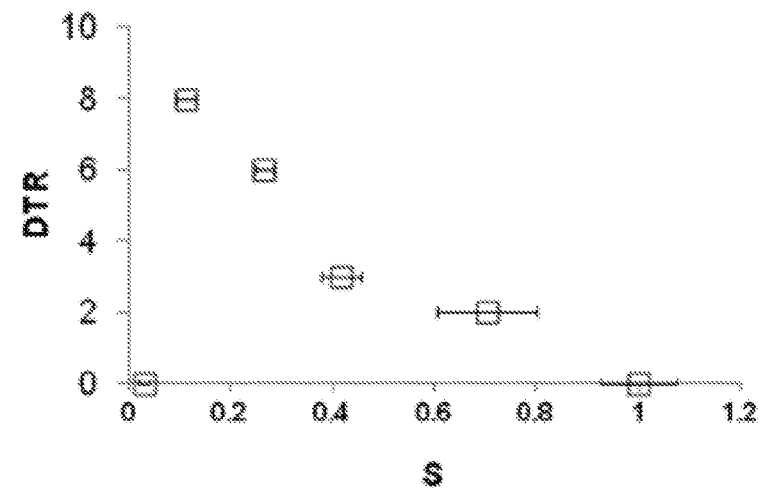
FIG. 8C is a graphical illustration representing the NHDF cell culture days to confluence recovery as a function of the pulsed electric exposed survival fraction cells.

FIG. 8A. shows the fraction of cells that survived first two hours after the pulsed electric field treatment. It is important to point out that part of these cells are still electroporated since complete membrane resealing process takes hours. To describe the probability of NHDF death, the Weibull distribution was used (FIG. 8B), as commonly utilized to describe the probability of bacteria cell death pulsed electric fields.

$$S = \exp(-N/a)^b \quad (1)$$

or alternatively, $$\ln(-\ln(S)) = b \ln N - b \ln a \quad (2)$$

where S is the survival fraction NDHF and N is the number of pulses applied to cell culture. The calculated Weibull distribution coefficients were b=0.72 and a=38.9. In addition, the NHDF culture recovery time to 100% confluence (days to recover-DTR) was investigated as a function of the survived cell fraction is shown on FIG. 8C.

To determine the recovery profile of NHDF cell culture at different time points after a single pulsed electric fields treatment, images were taken at various time points until cells 100% confluence was recovered. The results from the microscopic observations are shown in FIG. 9, as described below.

Figure 9:
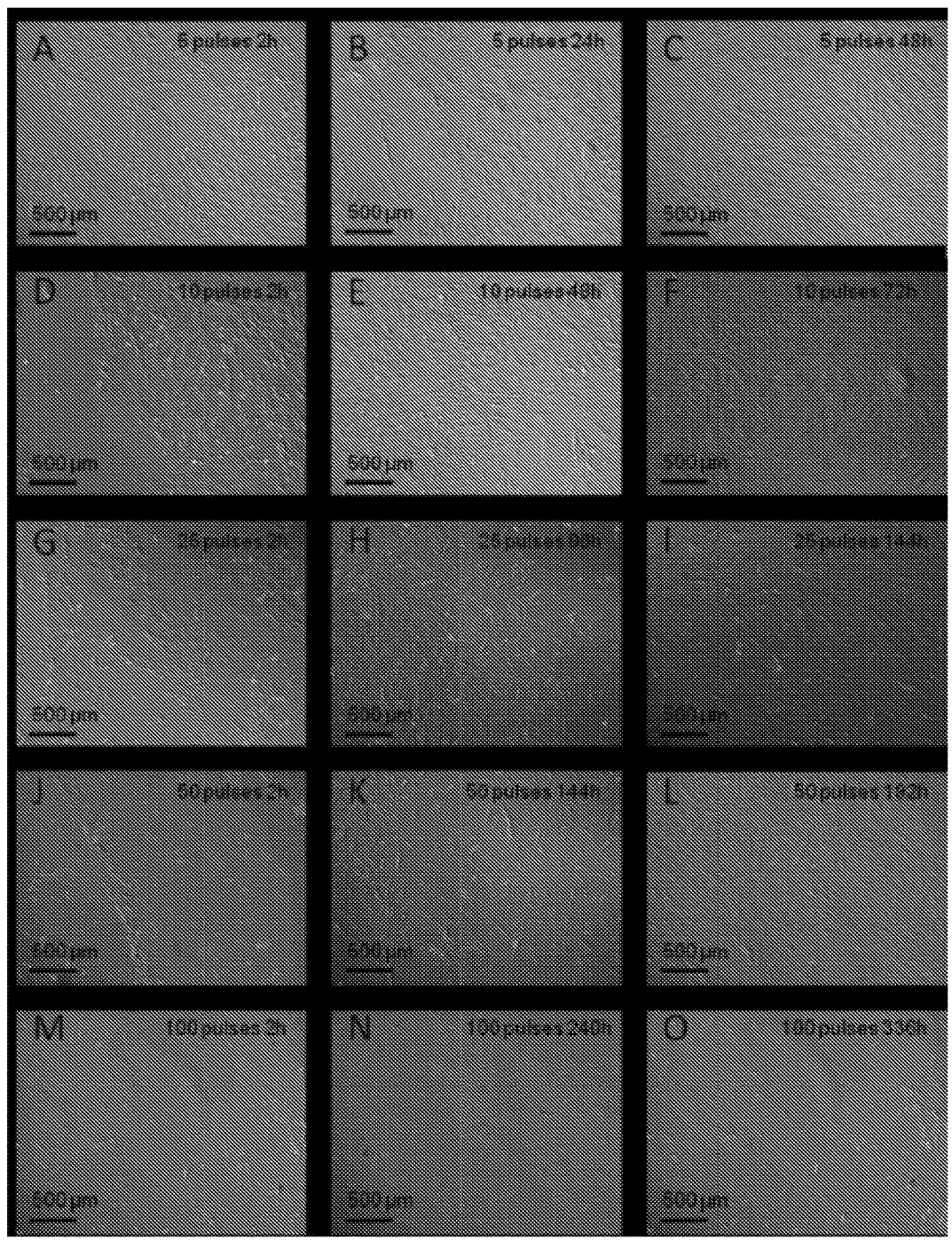
FIG. 9A-9O shows images representing NHDF cell culture recovery profiles at different time points after single pulse electric field treatment

FIG. 9.A,B,C show the recovery of the NHDF culture that was treated with 5 pulses of 150 V/m electric field, 70 µs duration pulses delivered at 1 Hz as 2 h, 24 h and 48 hours respectively after the treatment. It took 2 days for the culture to recover after 5 pulses treatments.

FIG. 9.D,E,F show the recovery of the NHDF culture that was treated with 10 pulses of 150 V/m electric field, 70 µs duration pulses delivered at 1 Hz at 2 h, 48 h and 72 hours respectively after the treatment. The culture fully recovered 72 hours after treatment. We used this protocol in the following IDPEF studies.

FIG. 9.G,H,I show the recovery of the NHDF culture that was treated with 25 pulses of 150 V/m electric field, 70 µs duration pulses delivered at 1 Hz at 2 h, 96 h and 144 hours respectively after the treatment. The NHDF cell culture recovered 6 days after the treatment.

FIG. 9.J,K,L show the recovery of the NHDF culture that was treated with 50 pulses of 150 V mm$^{-1}$ electric field, 70 µs duration pulses delivered at 1 Hz at 2 h, 144 h and 192 hours respectively after the treatment. The cell culture was fully confluent 8 days after the treatment.

Finally, FIG. 9.M,N,O show the recovery of the NHDF culture which was treated with 100 pulses of 150 V mm$^{-1}$ electric field, 70 µs duration pulses delivered at 1 Hz at 2 h, 240 h and 336 hours respectively after the treatment. From the 336 hours (2 weeks) observation in this experiment NHDF culture did not show any recovery after 100 pulses.

Fibroblast Proliferation and Cell Culture Recovery Under IDPEFs.

Figure 10:
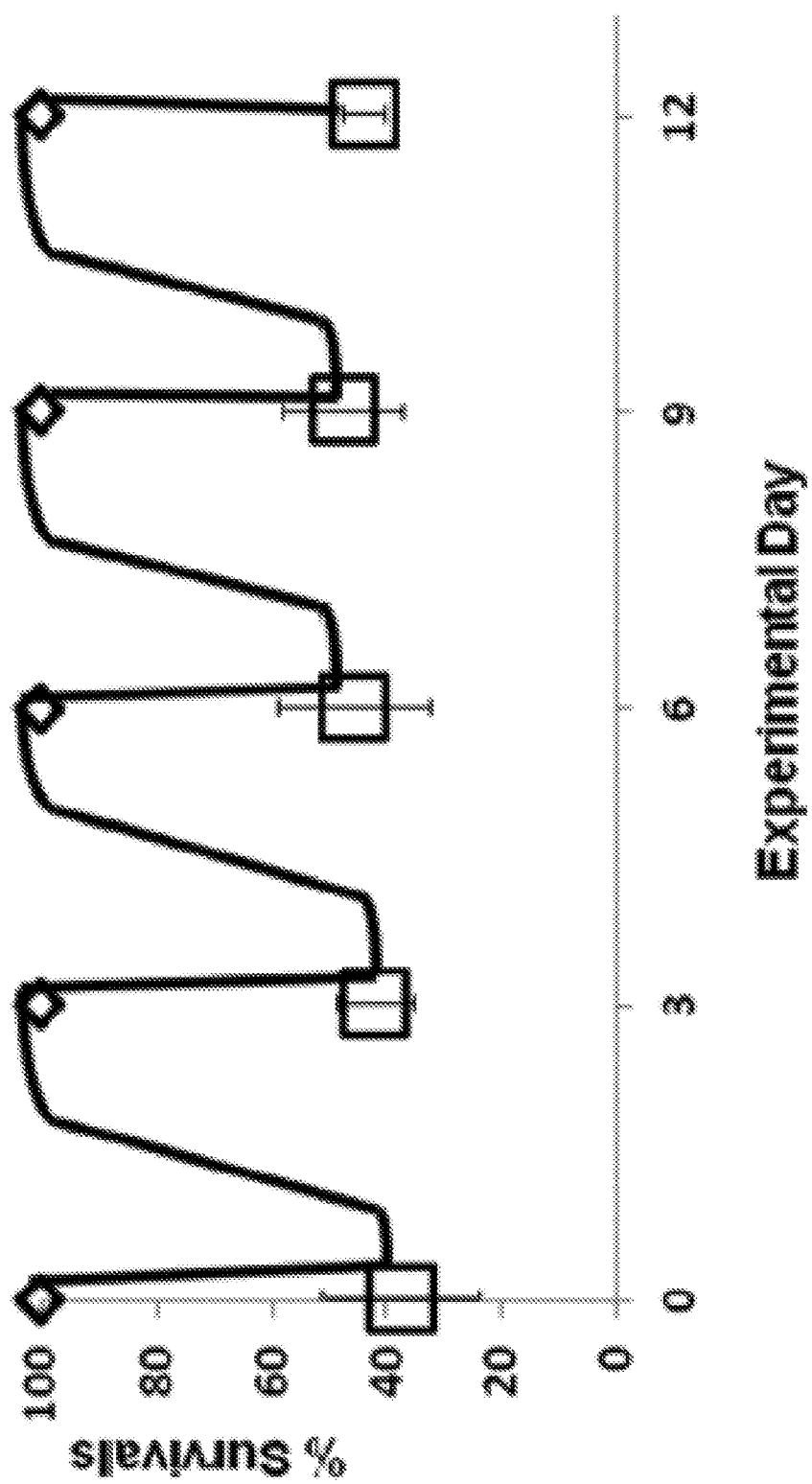
FIG. 10 is a graphical illustration of NHDF density control in culture using IDPEF.

To investigate the NHDF culture recovery profile under IDPEF, 10 pulses of 150 V/mm, 70 µs duration each at 1 Hz were applied every 72 h to the NHDF cultured in 6 well plates. As shown in FIG. 10, 43±4% of NHDF, which survive each pulsed electric fields treatment, recover to 100% confluent culture after 72 h, as measured by life cell count method. The line that describes cell concentration between the 100% and 43±4% confluence, or 3.1±0.2·10$^5$ ($C_{high}$ Cell ml$^{-1}$) and 1.4±0.2·10$^5$ ($C_{low}$ Cell ml$^{-1}$), was constructed using serial microscopic observations. The microscopic observations of treated cell cultures demonstrated that for the first 12 h after treatment cells show almost no proliferation. This is followed by a rapid proliferative phase that slows down approximately 48 hours the treatment. During the last 24 hours, the cells grow slowly to fill any empty space. Therefore, using this specific IDPEF protocol the NHDF was controlled in the confluence range between 43±4% and 100%.

Discussion

Proliferative scar formation can occur in wounds from many etiologies and is an important unsolved clinical problem. Many non-cutaneous clinical problems, such as tendon adhesions, bile duct strictures, cirrhosis of the liver, and glomerulonephritis are also the result of proliferative scarring. Unfortunately, Phase III trials of human TGF-β3 therapy, failed to demonstrate benefit in 2011, emphasizing the complexity of interactions between extracellular and cellular components during healing. Therefore, it seems likely that targeting single mechanisms may not be effective and external multi-target therapies are needed. Physical therapies help a potential to affect multiple targets by externally, well-controlled interventions.

In this work a novel way was introduced, compared to previous attempts, for controlling cell density and proliferation. Using IDPEF, this approach allows for precise targeting of desired tissues, affecting cell density locally without complex system effects. Since no animal model for proliferative scarring exists, a first step was made towards fibroblast density control by developing an IDPEF protocol in vitro. One goal of this study was to characterize NHDF cell death as a function of the applied pulsed electric field protocol. Previously, we introduced a theoretical study where we used a probabilistic approach to describe mammalian cell death by pulsed electric fields. To the best of our knowledge, this is the first experimental work that describes pulsed electric fields induced cell death using probabilistic methods. We characterized the dose response of NHDF culture in FIG. 7 and Table IV and used Weibull distribution to describe the probability of cell death as a function of number of pulses (FIG. 8). The Weibull distribution shape parameter and scale parameter were found to be 0.72 and 38.9, respectively.

Another goal was to investigate the NHDF culture recovery time after partial non-thermal pulsed electric fields.

Previously, non-thermal irreversible electroporation was used as an efficient tissue ablation method with set parameters defining only the degree of total cell destruction in the treated area. By contrast, this work suggests that cell density can be controlled by IDPEF and only a fraction of cells may be killed, with surviving cells capable of performing their biological function. Therefore, it is advantageous to characterize the recovery rate of cells under different treatment conditions. FIG. 9 illustrates NHDF culture recovery under different pulsed electric fields treatment conditions, indicating that a range of 5-50 pulses allowed the survived cells to recover in 2-8 days after the treatment. In contrast, 100 pulses inactivated 97% of cells and no cell proliferation or recovery of the survived cells was observed.

Using data collected from the NHDF cell culture response to a single pulsed electric field exposure, a protocol was designed for cell density control in vitro by IDPEF. NHDF cultures were exposed to IDPEF every 72 hours. In this experiment, it was determined that the minimum percentage of cells needed to survive so as to recover to confluence in 72 hours was 43±4%, shown in FIG. 10. Treatments were repeated 5 times to investigate the effects of IDPEF on the cell culture. Results suggested that IDPEF can maintain cell density in the prescribed range, if the inactivation kinetics and recovery rates are known. Since the current study is the 2D cell culture surface, and 3D the behavior of the system in vivo may be different, additional in vitro 3D models may be needed for further understanding of the effect of the matrix on cell survival and migration.

In conclusion, here we introduce a new chemical-free method for fibroblast density control in culture by IDPEF, which cause irreversible damage to cell membranes. Using 5-100 pulses with electric field strength of 150 V mm$^{-1}$, pulse duration 70 µs, and frequency of 1 Hz, we investigated the effects of pulsed electric field application on growth, death, and regeneration of normal human dermal fibroblasts in culture. We found that the fraction of fibroblasts that survive depends on the number of pulses applied and follows a Weibull distribution. We have successfully developed an IDPEF protocol that controls fibroblasts density in culture. Specifically, through application of IDPEF every 72 hours for 12 days, we maintain a normal human dermal fibroblast density in the $3.1\pm0.2\cdot10^5$-$1.4\pm0.2\cdot10^5$ Cell ml$^{-1}$ range. Our results suggest that IDPEFs may prove useful as a non-chemical method for fibroblast density control in human wound healing.

For many attaching cell types, 100% confluence in vitro suggests inhibition of proliferation and growth, possibly due to contact inhibition. In vivo, however, cell proliferation and density is directed by multiple, complex chemical, mechanical and electrical pathways. Although these mechanisms are very tightly regulated, aberrations of the control mechanisms lead to diseases, such as cancer and fibroses. As such, external intervention may return balance to the system by applying IDPEF in vivo to control the cell density by partial irreversible electroporation of cells. In this manner, malregulated fibroblast apoptosis, which is thought to be one of the reasons for proliferative scarring, may be compensated.

Special electrically active bondage for the in vivo applications may be used to deliver IDPEF only to the prescribed areas of the wound. Electrically active biomaterials, which deliver low amplitude pulsed electric fields for stimulation, have been already reported in addition to methodologies for achieving special control of electric field distribution in tissues. Additional in vivo studies, however, may be needed to address the level of the partial cell ablation in tissues that still preserves the critical functions, such as the infection barrier, as well as provide an understanding whether non-thermal irreversible electroporation can selectively ablate specific cell types and spare non-target cells in heterogeneous tissues.

Example II

Figure 11:
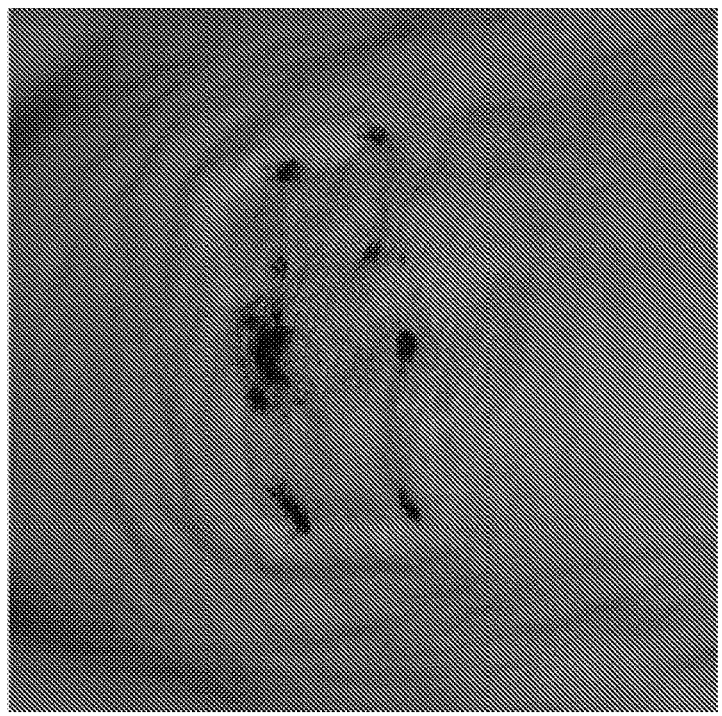
FIG. 11 is an image showing a process of administration of electric field pulses to rat skin.
Figure 11:
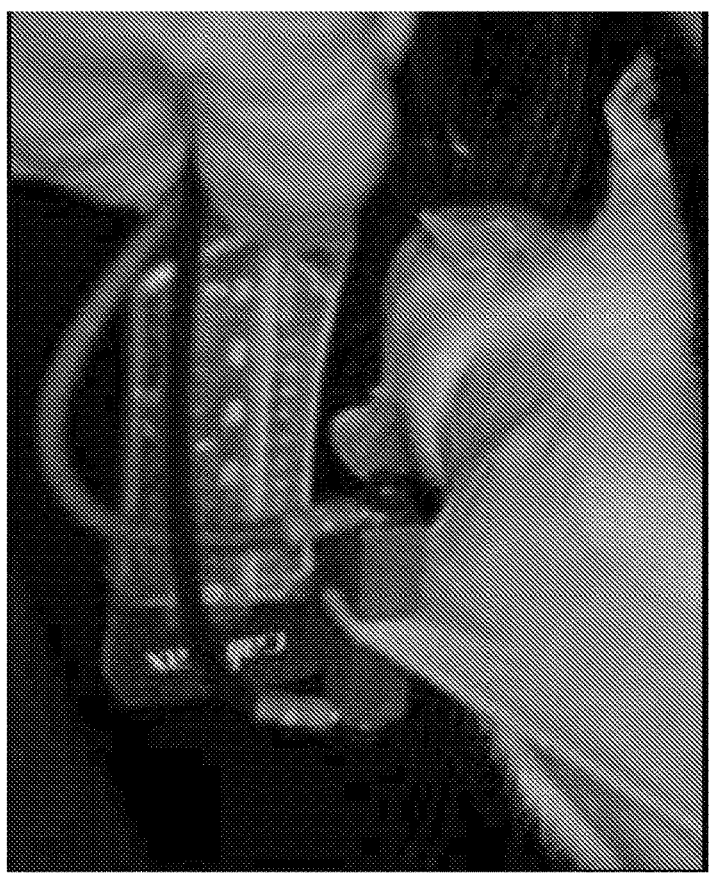

To explore the potential use of non-thermal pulsed electric fields for regenerative medicine research, outcome of tissue regeneration following pulsed electric fields ablation were investigated in a murine animal model. Using contact electrodes, surface areas of a dorsal skin-fold of Sprague Dawley female rats were treated with non-thermal pulsed electric fields (FIG. 11). Results indicate the preservation of blood supply to ablated skin in rats followed by regeneration of the epidermal layer, skin appendages and the striated deep muscle layer, two months post-treatment. Results also showed increased collagen and ellastin fiber density in the treated skin, suggesting advantageous use for basic regenerative medicine and developmental biology research.

Methods
Animals

Six-week old female Sprague-Dawley rats (~200 g, N=23) were obtained from Charles River Laboratories (Wilmington, Mass.). The animals were housed in individual cages with access to food and water ad libitum with food and water provided ad libitum, and were maintained on a 12-hour light/dark cycle in a temperature controlled room. All animal procedures were approved by the subcommittee on Research Animal Care (IACUC) of the Massachusetts General Hospital and were in accordance with the guidelines of the National Institutes of Health (NIH).

Pulsed Electric Fields

Prior to electric field pulse treatment, the animals were anesthesized with isoflurane and shaved on the dorsal surfaces. The skin of the whole torso was clipped and treated with depilatory cream (Sally Hansen® Div. Del Laboratories, Inc., Farmingdale. N.Y.). Subsequently, a designated area was subjected to electroporation using contact electrodes with a surface area of 1 cm$^2$ and separation of 2 mm. Electric field pulse specifications included four series of 45 pulses, with pauses of 30 sec included between treatment series. Square pulses were typically 250 V/mm in amplitude and 70 µs in duration, administered at a frequency of 2 Hz using a BTX 830 pulse generator (Harvard Apparatus Inc, Holliston Mass., USA). Currents were measured in vivo using PicoScope 4224 Oscilloscope with Pico Current Clamp (60 A AC/DC) and analyzed with Pico Scope 6 software (Pico technologies Inc., UK). To evaluate temperature effects of the electric field pulses, heat transfer analysis was performed with MATLAB, R2009b (MathWorks, Natick, Mass., USA). To construct a function that describes current density as a function of pulse numbers, a symbolic regression analysis was performed with Eureqa II (Cornell Creative Machines Lab).

Burn Injury

Before the creation of third-degree burns, the animals were anesthesized with isoflurane and shaved on the dorsal surfaces. Burns were incurred by pressing the ends of two pre-heated (≥95 C) brass block against opposite sides of a raised dorsal skin fold from the rats back for 10 seconds, resulting in a non-lethal, full-thickness, third-degree burn measuring approximately 1 cm$^2$. Burn injury and the electric field pulses were administered on the same animals (2 cm apart).

Laser Doppler Scanning.

A laser Doppler imager (Moor Instruments, Wilmington, Del.) was used to assess blood flow. The laser Doppler source was mounted on a movable rack exactly 20 cm above the back of the rat after the animal was anesthetized and restrained on the underlying table. The laser beam (780 nm) reflected from moving red blood cells in nutritional capillaries, arterioles, and venules was detected and processed to provide a computerized, color-coded image. By using image analysis software (Laser Doppler Perfusion Measure, Version 3.08; Moor Instruments), mean flux values representing blood flow were calculated from the relative flux units for the areas corresponding to the dorsum of the mice. Baseline images were obtained from each rat before burning. Rats were treated by electric field pulses or burn, and serial laser Doppler images were obtained post treatment. The entire procedure was performed under warm conditions.

Histopathological Analysis

Specimens were harvested after 24 h, 1 week, 3 weeks, and 2 months following the initial procedure. Five animals were euthanized for each time point. Three animals were used as controls. Skin samples were fixed with 10% formalin, embedded in paraffin, and processed for staining with hematoxylin and eosin. Tissues were processed and stained by Rodent Histopathology Core at Harvard Medical School. Slides were evaluated by an experienced dermatopathologist. Samples were imaged using Nikon Eclipse 800 and SPOT (version 4.0.9) camera (Diagnostic Instruments Inc, MI, USA).

Inflammation Infiltration Analysis

To quantify the inflammatory reaction to the panniculus carnosus of the ablated areas, granulocytes were counted manually by two independent investigators. Three fields of view were imaged from slides for each animal (5 animals per time point). Cell counts were conducted using ImageJ (NIH, MD, USA).

Statistical Analysis

A statistical toolbox in MATLAB, R2009b (MathWorks, Natick, Mass., USA) was used for statistical analysis. To fit the function for the current density changes over the number of pulses non-parametric regression analysis with Eureqa II (Cornell Creative Machines Lab, USA) was used. Five searches were performed for 4.5 h and ~1.2M generations of functions. The chosen function showed the best error to complexity ratio. The confidence for the chosen function was: stability 8.64%, maturity 90.2%.

Thermal Effects Analysis

Figure 12B:
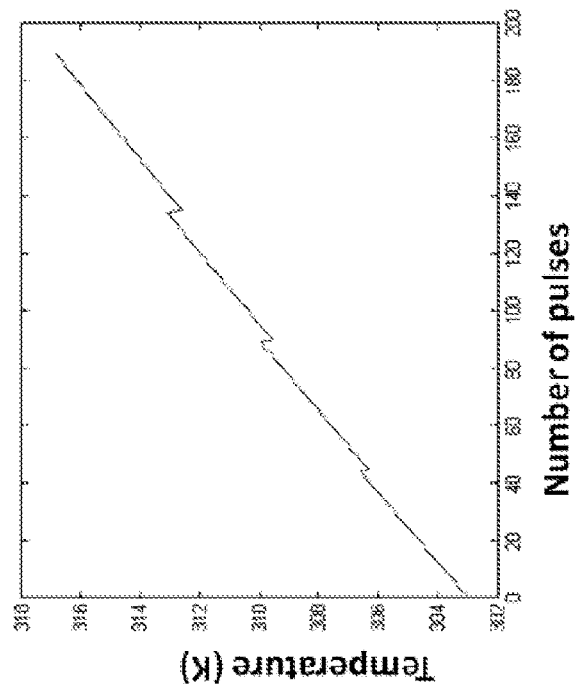
FIG. 12B is a graphical illustration of a modeled temperature increase of skin as a function of electric field pulses.
Figure 12A:
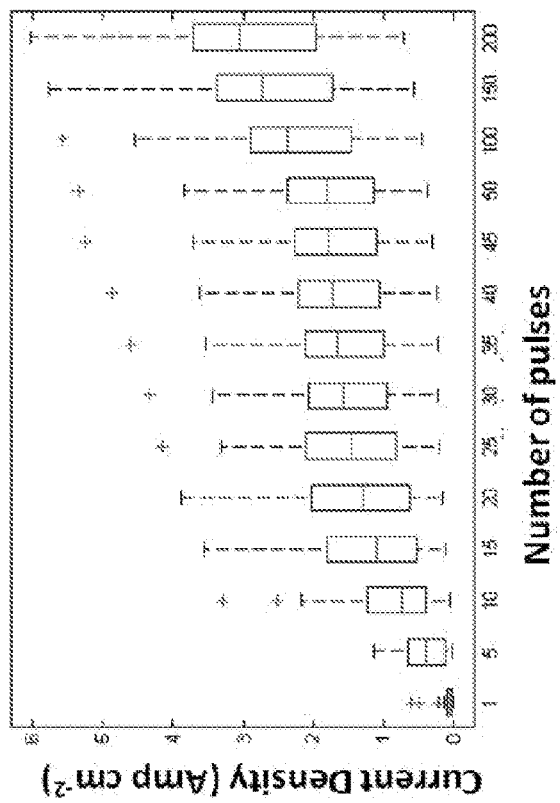
FIG. 12A is a graphical illustration indicating increased current density with number of electric field pulses.

To estimate the thermal effects of electric field pulses, the current densities generated during treatment were measured during (FIG. 12A), where an increase in current density indicates an increase in tissue conductivity, which usually results from cell membrane rupture. An analytical solution of electro-thermal processes was then performed by calculating the heat supplied to the skin by each electric pulse using:

$$Q_n = I_n V t_p \quad (1)$$

where $Q_n$ (Joule) is the heat supplied to the skin by a single pulse (n); $I_n$(Amp) is the current during the pulse number (n), V (Volt) is the applied voltage. The temperature increase of a treated skin section, immediately after the application of field E was calculated according to:

$$T_{pn} = \frac{Q}{mc_p} + T_{in} \quad (2)$$

where m (gram) is the mass of a skin section on which electric fields are applied; $c_p$ is the heat capacitance of skin; $T_{in}$ (K) is the temperature of the treated section of skin immediately before the treatment. To calculate the temperature of the skin during cooling between pulses, we used Lumped Capacitance Heat Conduction approximation as follows:

$$T_{cn} = T_{env}(T_{pn} - T_{env})e^{-B_iF_o} \quad (3)$$

where $T_{cn}$ (K) is the temperature of the treated skin after a cooling period which followed pulse number (n); $T_{env}$ (K) is the environmental temperature; $B_i$ is the Biot number and $F_o$ is the Fourier number. Solving equations 1-3 simultaneously, the temperature increase of the treated rat skin during the IRE procedure (FIG. 12B) was calculated.

Results

Figure 13:
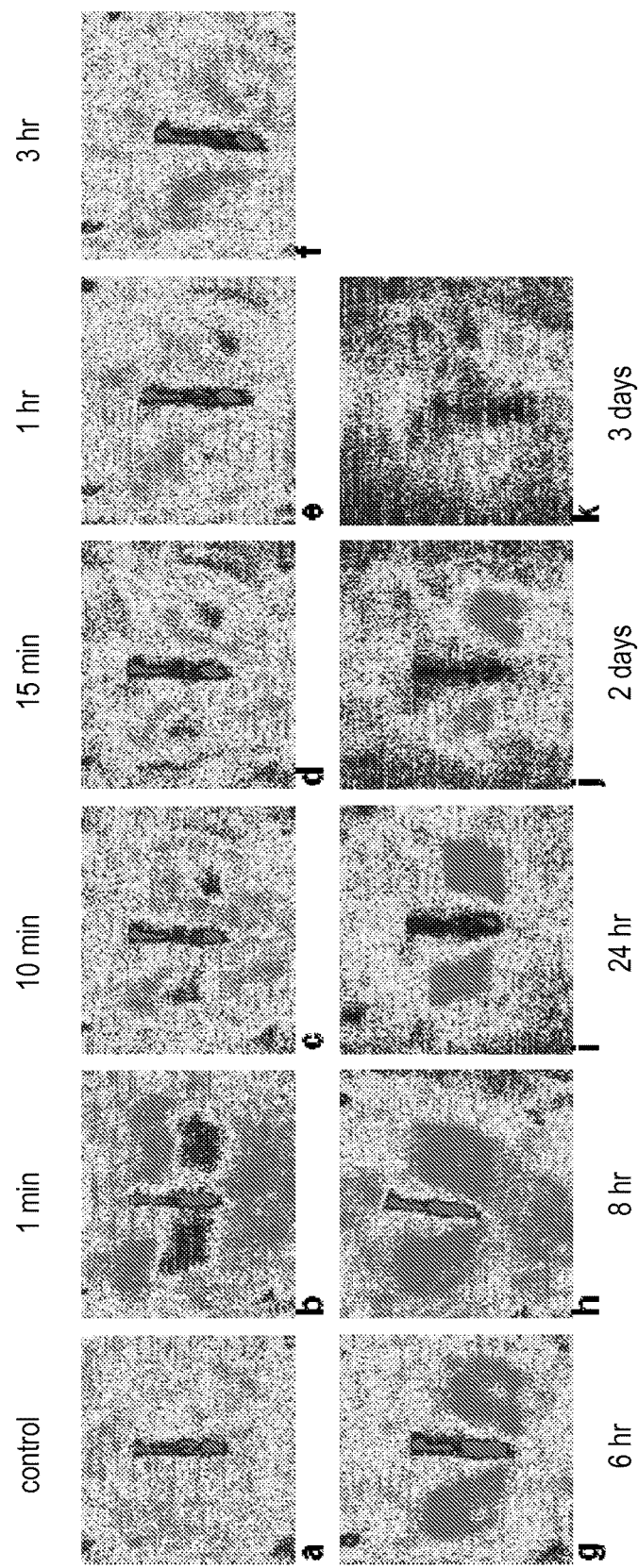
FIG. 13 is a time series of images from ablated rat skin captured using laser Doppler scanning.
Figure 14:
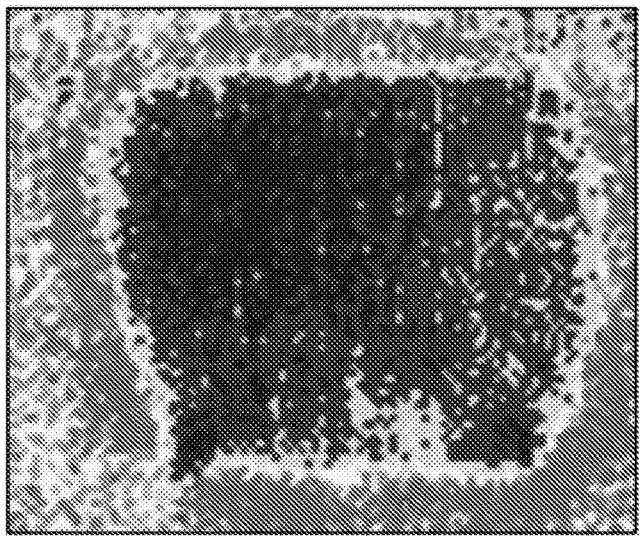
FIG. 14 is a graphical illustration of differences in blood perfusion of a skin area treated with pulsed electric fields compared to a third degree burn.
Figure 14:
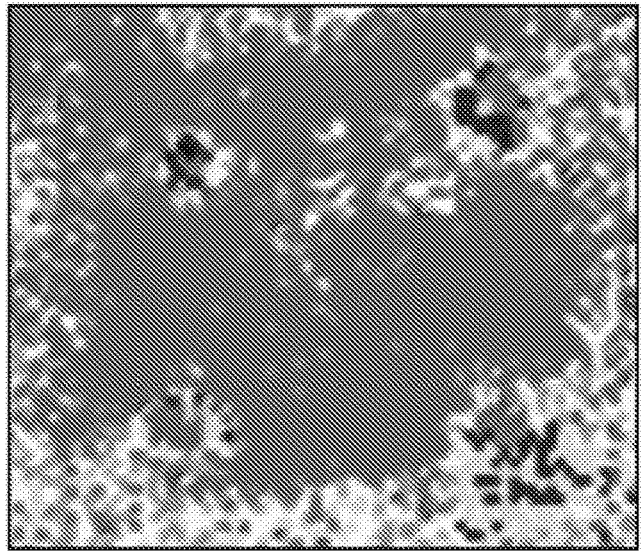

To evaluate the effects of electric field pulses on skin blood supply, we measured blood perfusion at the treated areas using laser Doppler imaging (LDI), reported as perfusion unit (flux) ratio of the treated area flux to the untreated area. Third degree burn injury of similar area was used as positive control. Our data, described in FIG. 13, indicates that electric field pulses cause a delayed and significant vasoconstriction at the level of pre-capillary arterioles for the first 3 hours after treatment (FIG. 13 b-f). At later times (FIG. 13 g-k), an increase in blood flow can be seen, with a maximum at 8 hours after treatment. This belated increase in perfusion leads to a significant flow of inflammatory cells to the treated area. These blood perfusion findings are important as they demonstrate that ablation using electric field pulses causes a very localized and dynamic response. Most notably, these results show that electric field pulses preserve the micro-vascular architecture and function, which allows for full and timely recovery of perfusion, clearance of low-grade inflammatory cellular debris followed by effective tissue regeneration that retains normal skin morphology without scar formation. A marked difference after 24 hours in the perfusion pattern after electric field pulse treatment may be seen compared to a third degree burn in FIG. 14, where the flux ratio decreased to 0.3. In contrast, treatment with electric field pulses showed increase in flux ratio in the treated areas to 1.6 indicating a preservation of blood and hyperemic response. (FIG. 14A and FIG. 14B).

Figure 15:
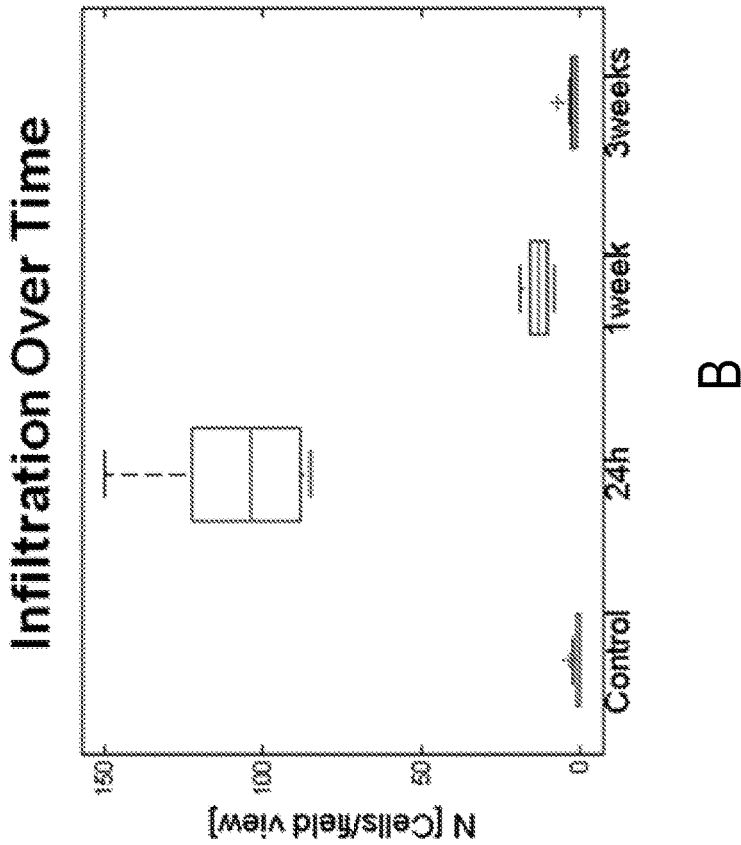
FIG. 15 is a graphical illustration of dynamic granulocytes infiltration into an area treated with pulsed electric fields.

Histopathological analysis of skin samples, harvested 24 after electric field pulse treatment, demonstrated granulocytic infiltration into the IRE ablated area after treatment (FIG. 15A). These infiltrations were temporary and resolved by 3 weeks (FIG. 15B). The preservation of blood supply to the areas with electric field pulses is consistent with previous reports that showed sparing of large blood vessels and tissue micro-architecture. In contrast, third-degree burns completely destroyed the tissue structure, eliminated blood supply and led to full tissue necrosis. It is important to emphasize that the exact mechanisms of cell death induced by pulsed electric fields are not completely understood, as both necrosis and delayed apoptosis at the damages sites have been reported.

Figure 16:
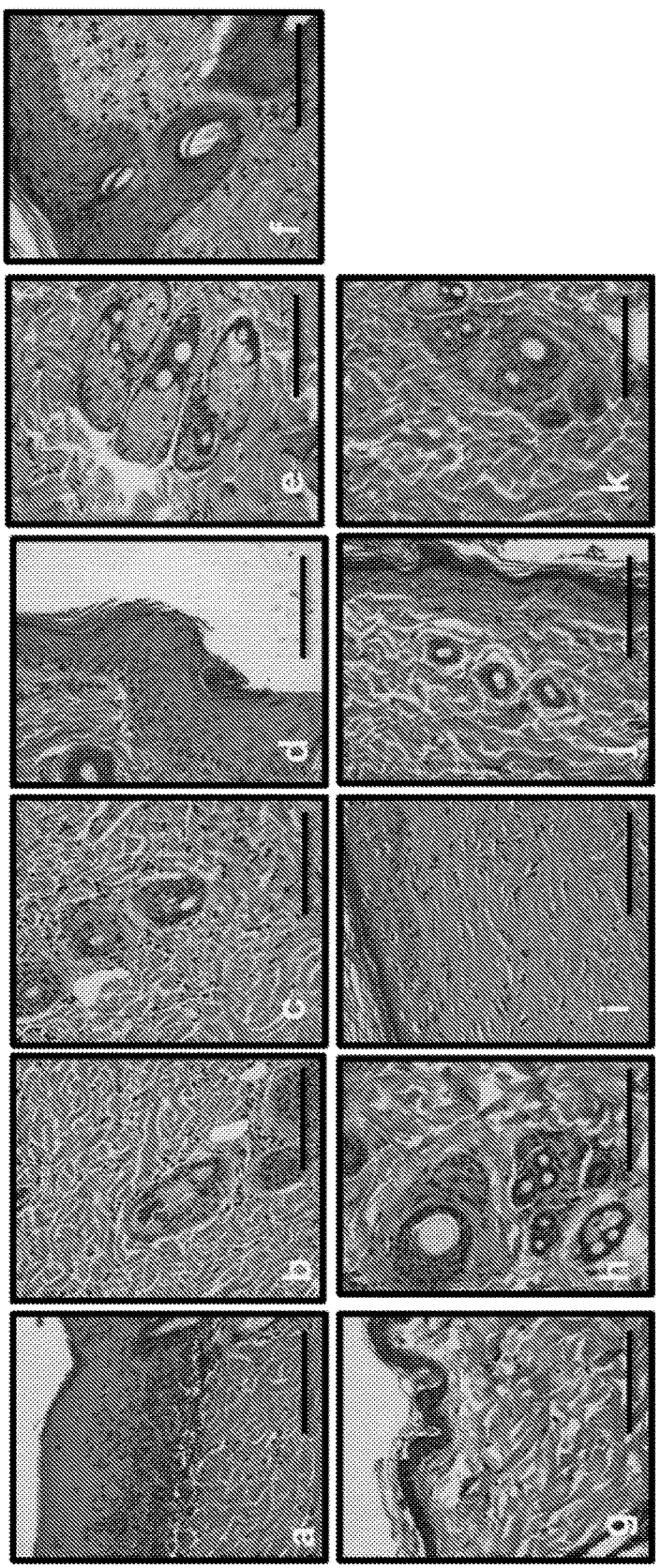
FIG. 16 shows images of histopathological analysis of skin damage and regeneration by use of pulsed electric fields.
Figure 17:
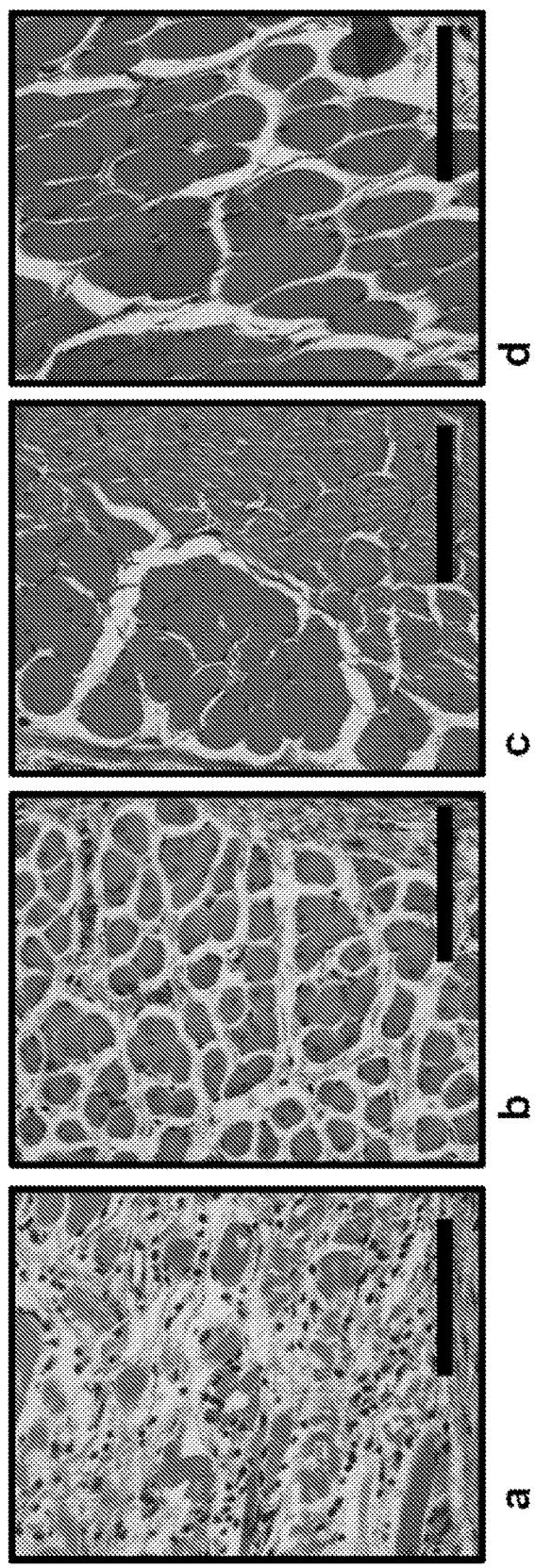
FIG. 17 shows images from histopathological analysis of panniculus carnosus damage and regeneration by use of pulsed electric fields.

Immediate gross examination of the area treated with pulsed electric fields revealed edema and hyperemia. Six hours post-treatment, initial infiltration of the panniculus carnosus with inflammatory cells was observed. After twenty-four hours, the edema had subsided. Microscopic examination demonstrated rupture and scab formation in the epidermal layer (FIG. 16 a), fusion and death of sebaceous glands (FIG. 16 b) and hair follicles (FIG. 16 c). The panniculus carnosus showed disintegration and death of skeletal muscle fibers as well as massive infiltration of granulocytes to the ablated area (FIG. 17 a).

The morphological observations made at 24h after injury include: 1) severe damage to muscle fibers; 2) degranulation of mast cells; 3) swelling of nerve fibers; 4) intact and undamaged vasculature; 5) cell fusion and apoptosis in sebaceous glands; 6) damage to the hair follicles, with delayed maturation of up to 72 h. Although minor inflammation at the treated site was still observed one week after the treatment, the regenerating muscle showed high proliferative activity, as evident from the multiple muscle fibers with centrally localized nuclei in the center. After three weeks there were no remaining histological signs of inflammation at the treated sites. Histologically, muscle fibers looked regenerated.

Unlike the eschar of a third-degree burn, skin ablated with pulsed electric fields did not fall after one week. On the contrary, one week after injury, we observed complete regeneration of the epidermal layer (with multiple cell layers), (FIG. 16 d), re-growth of sebaceous glands (FIG. 16 e) and hair follicles (FIG. 16 f), diminished granulocyte infiltration in the panniculus carnosus, (FIG. 15B) as well as multiple regenerating skeletal muscle fibers (with centrally located nuclei) (FIG. 17 b).

Two months after injury, the epidermis at the treated site regenerated to the same thickness of 1-2 cell layers as appearing in the non-treated skin (FIG. 16 g and j). Sebaceous glands and hair follicles regenerated to the same morphology as they appear in the untreated skin dermis (FIG. 16 h, j, k). Third-degree burns, however, did not show regeneration of sebaceous glands and hair follicles at this time and scar formation was evident (FIG. 16 i). Moreover, the epidermal layer was still composed of multiple layers, different from 1-2 cell layer in the untreated and post-IRE regenerated epidermis (FIG. 16 g, i, j). Two months post-treatment, fiber fusion and migration of the nucleolus to the fused fibers periphery was observed in the panniculus carnosus (FIG. 17 c, d). Granulation tissue or fibrosis in the IRE-treated areas were not observed throughout our study. Our data is in agreement with previous studies showing that non-thermal pulsed electric fields have the unique ability to eliminate cells, while preserving blood supply and tissue microarchitecture at the treated sites.

Figure 18:
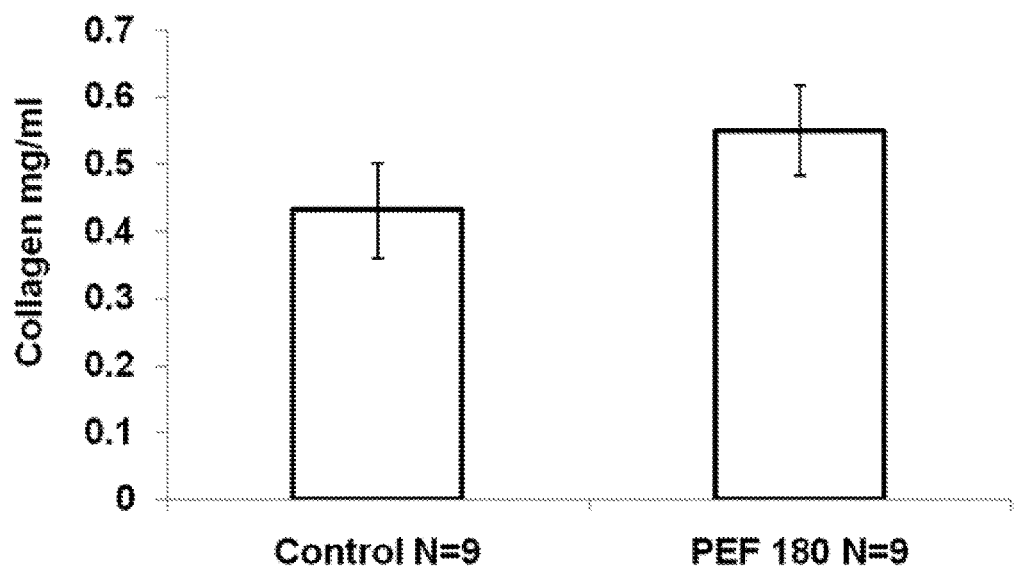
FIG. 18 is a graphical illustration of the effects collagen density using pulsed electric field treatment.
Figure 18:
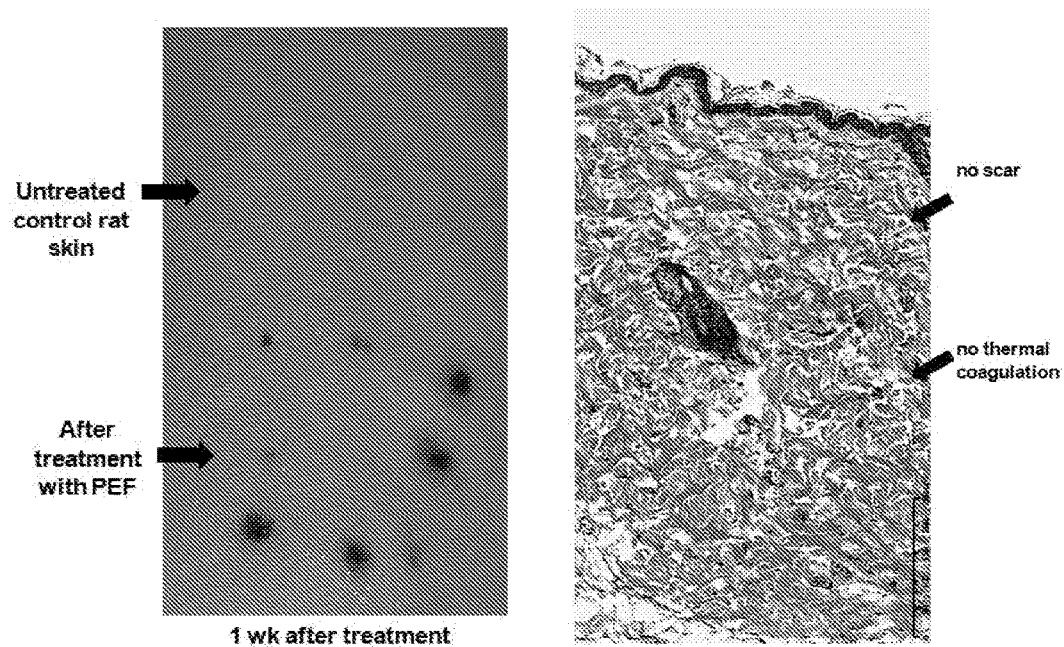
Figure 19:
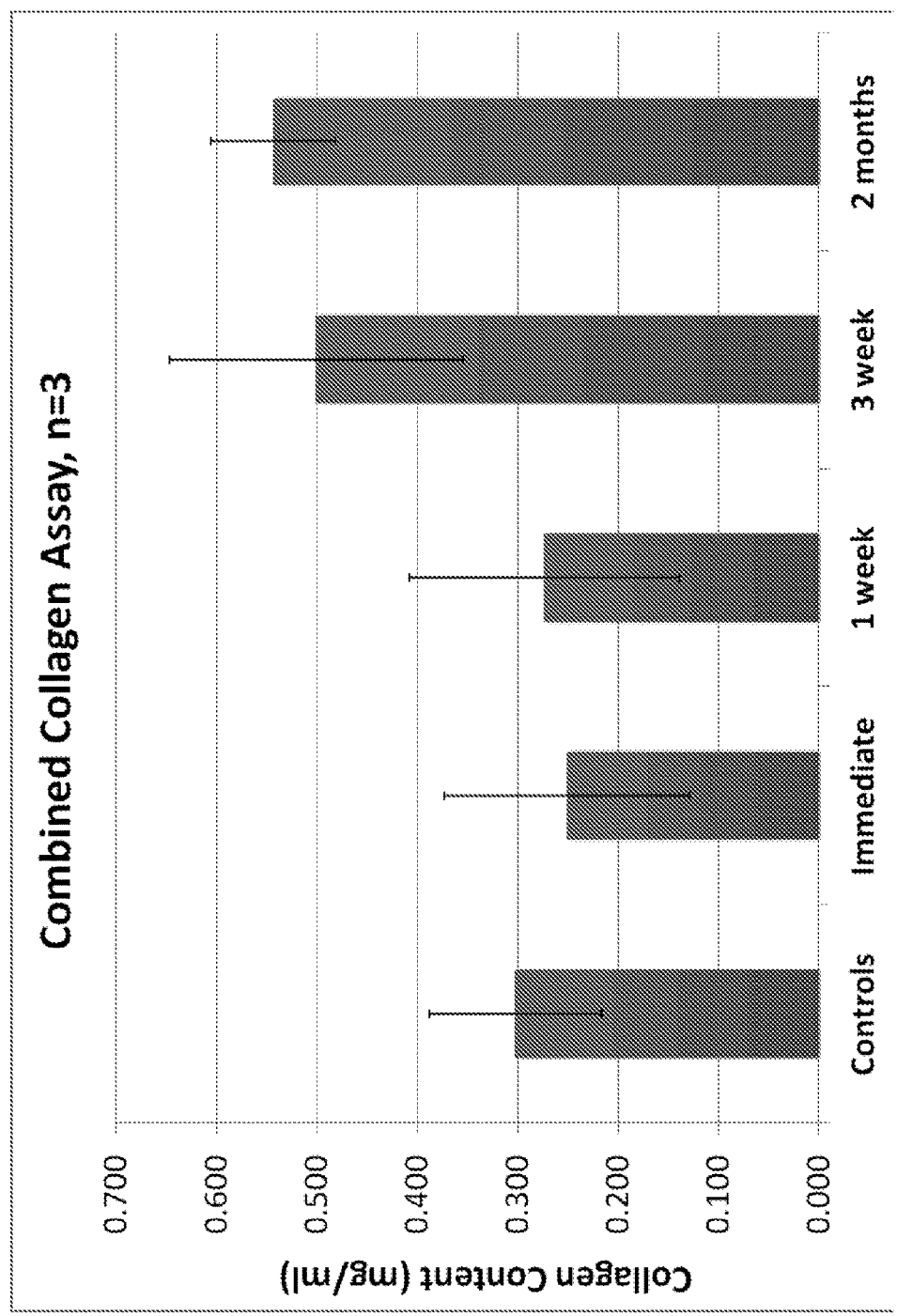
FIG. 19 is a graph showing collagen content resulting from pulsed electric field treatment.

Histopathological analysis also showed increased collagen and elastin fiber density in the treated skin. For biochemical analysis, collagen assays were performed. The collagen content in the PEF treated skin was 1.4±0.2 (N=9) higher than in the age matched controls 3 weeks after treatment, shown in FIG. 18. Therefore, after pulsed electric fields treatment using 180 pulses, skin appeared visually better, without the presence of erythema, dyspigmentation, scarring, scabbing, or downtime. FIG. 19 shows results from collagen assays at different time points compared to the control.

Therefore these results show pulsed electric fields produce transiently altered skin perfusion and acute cellular death with a local inflammatory reaction. Since thermal modeling results (FIG. 12B) showed that skin temperature does not generally increase more than 10K during treatment, damage to the skin is mostly delivered by non-thermal effects. However, complete skin and panniculus carnosus tissue regeneration without signs of fibrosis can be observed over time. These findings are strikingly different to third-degree burn injuries, which undoubtedly lead to scar formation. Although the mechanisms of scarless tissue regeneration after pulsed electric fields remain unclear, we hypothesize that preservation of blood supply and tissue microarchitecture by non-thermal pulsed electric fields may explain the complete scarless skin regeneration. We believe that preservation of blood supply allows the treated areas to be supplied with oxygen, nutrients, signaling molecules and cells, while in thermal burns blood vessels thrombose and collapse; thus, preventing the transport of nutrients and regeneration components to the injured site.

Therefore, pulsed electric fields offer a highly promising strategy in tissue regeneration with a broad spectrum of clinical applications, such as wound healing, skin rejuvenation, tumor ablation, and so on. Further studies aimed at dissecting the mechanisms responsible for cellular ablation using non-thermal pulsed electric fields and clinically usage may be warranted.

Example III

Emerging resistance of bacteria to multiple drugs is one of the most significant challenges for wound care and new interventions are needed for wound disinfection. Here we report on a new, physical disinfection method using antiseptic pulsed electric fields applied externally on infected wounds. We show that pulsed electric fields can reduce by more than 4 Log 10 the load of multidrug resistant *Acinetobacter baumanni* infection of the full thickness third degree burn, as detected by bioluminescent imaging. Using numerical, finite elements models we show that pulsed electric fields deliver non-thermal, homogeneous full thickness treatment of the burn injury. The reported models will be extremely useful for further translation of the pulsed electric fields technology to clinics, as it provides the essential tools for electrode and treatment protocol planning. We believe that antiseptic pulsed electric field technology will provide a completely new intervention platform for multiple novel antibacterial strategies.

Materials and Methods

Animal Research

C57BL/6 4 month-old, females mice (~30 gr) were purchased from Charles River Laboratories (Wilmington, Mass.). The animals were housed in cages, 5 animals per cage, with access to food and water ad libitum, and were maintained on a 12-hour light/dark cycles in a temperature-controlled room. All surgery was performed under ketamine (100 mg/kg) and xylazine (10 mg/kg) anesthesia, and all efforts were made to minimize suffering.

Bacteria Culture

The bioluminescent pathogenic *Acinetobacter baumanii* ATCC BAA 747 (ATCC, Manassas, Va.) gram (−) bacteria strain was used. The bioluminescence genes (luxCDABE operon), originally cloned from *P. luminescens*, contained the luxAB genes that encode the luciferase enzyme, which catalyzes the light-emitting reaction and the luxCDE genes that encode an enzyme complex that synthesizes the luciferase substrate. The luxCDABE operon contained in plasmid pMF 385, a stable genetic reporter in the gram (−) organisms, was introduced into the clinical *A. baumannii* strain by following mostly standard molecular cloning protocols. Bacteria cells were grown overnight in brain heart infusion (BHI) at 37° C. with 100 rpm orbital shaking. The optical density at 600 nm was measured by a spectrophotometer (Thermo Scientific, Waltham, Mass.), OD600=0.8, corresponding to 108 colony forming units (CFU)/ml. The cells were washed and re-suspended in PBS (Dulbecco) and used at a density of 1×108 CFU/mL for the in vivo experiments.

Burn Injury

Before the creation of third-degree burns, the animals were anesthetized with ketamine/xylazine and their fur was clipped along the dorsal surface. Burns were incurred by dorsal skin surface contact with brass blocks (surface area 1 cm$^2$) pre-heated to 100° C. for 10 seconds, resulting in a non-lethal, full-thickness, third-degree burn measuring approximately 1 cm$^2$. One burn was created per animal. Immediately after the creation of the burns, the mice were resuscitated with Intraperitoneal (IP) injections of 0.5 ml sterile saline (Phoenix Scientific Inc., St. Joseph, Mo.) to prevent dehydration.

Burn Infection Model

Bacterial infection took place as described by Ha and Jin ("Expression of the soxR gene of *Pseudomonas aeruginosa* is inducible during infection of burn wounds in mice and is required to cause efficient bacteremia", *Infect Immun* 67, 5324-31, 1999). The burns were allowed to cool for five minutes. Subsequently, a 40 µl suspension of *A. baumannii*, ATCC BAA 747 including the luxCDABE operon, in sterile PBS containing 108 cells was inoculated onto the surface of each burn with a pipette tip. The drop was then smeared onto the burn surface with an inoculating loop. The mice were imaged with the luminescence camera, as described in the following section, immediately after application of the bacteria and thirty minutes after the infection to ensure that the bacterial inoculum applied to each burn was consistent.

Pulsed Electric Field Disinfection

A designated area was subjected pulsed electric field treatment using contact electrodes with a surface area of 1 cm$^2$. Pulses were delivered using a BTX 830 pulse generator (Harvard Apparatus Inc, Holliston Mass., USA). Currents were measured in vivo using a PicoScope 4224 Oscilloscope with a Pico Current Clamp (60 A AC/DC) and analyzed with Pico Scope 6 software (Pico technologies Inc., UK). PEF settings included a 2 mm gap between electrodes, an applied voltage of 1000 Volts in group 1 and 500 Volts in group 2, 70 µs pulse duration, 1 Hz pulse frequency, and 80 pulses. The pulses were delivered in two groups of 40 pulses with a five-minute interval between groups to allow bioluminescence imaging for each dose of 40 pulses. To evaluate potential temperature effects of pulsed electric fields, heat transfer analysis was performed with QuickField Professional 5.10 (Terra Analysis, Denmark).

Bioluminescent Imaging of Bacterial Load

The bioluminescent imaging system (Hamamatsu Photonics KK, Bridgewater, N.J.) consists of an intensified charge-coupled-device camera mounted in a light-tight specimen chamber fitted with a light-emitting diode—a setup that allowed for a background grayscale image of an entire mouse to be captured. In the photon-counting mode, an image of the light emitted from the bacteria was captured by using an integration time of two minutes at a maximum setting on the image-intensifier control module. Using the ARGUS software (Hamamatsu), the luminescent image was presented as a false-color image superimposed on the grayscale reference image. The image-processing component of the software calculated the total pixel values (in relative luminescence units [RLU]) from the luminescent images of the infected wound area. Previously, we have correlated the luminescence readout of *A. Baumannii* contaminated burns with CFU. Imaging was performed immediately after the injury, 30 min after the infection, after 40 pulses, after 80 pulses, and 3 hours after pulsed electric field treatment.

Numerical Modeling

Numerical solutions for electric field distribution in skin and the thermal effects of electric fields were performed in QuickField (Terra Analysis, Denmark).

Statistical Analysis

Statistical analysis was performed with toolbox in MATLAB, R2009b (MathWorks, Natick, Mass., USA). The error bars showed the standard deviation of the mean.

Results

Figure 20:
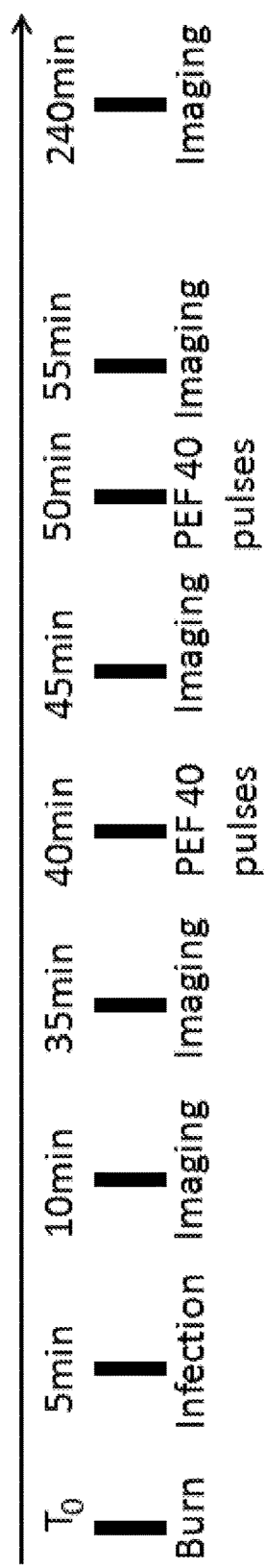
FIG. 20 is a timeline schematic of a burn would disinfection experimental design.
Figure 21:
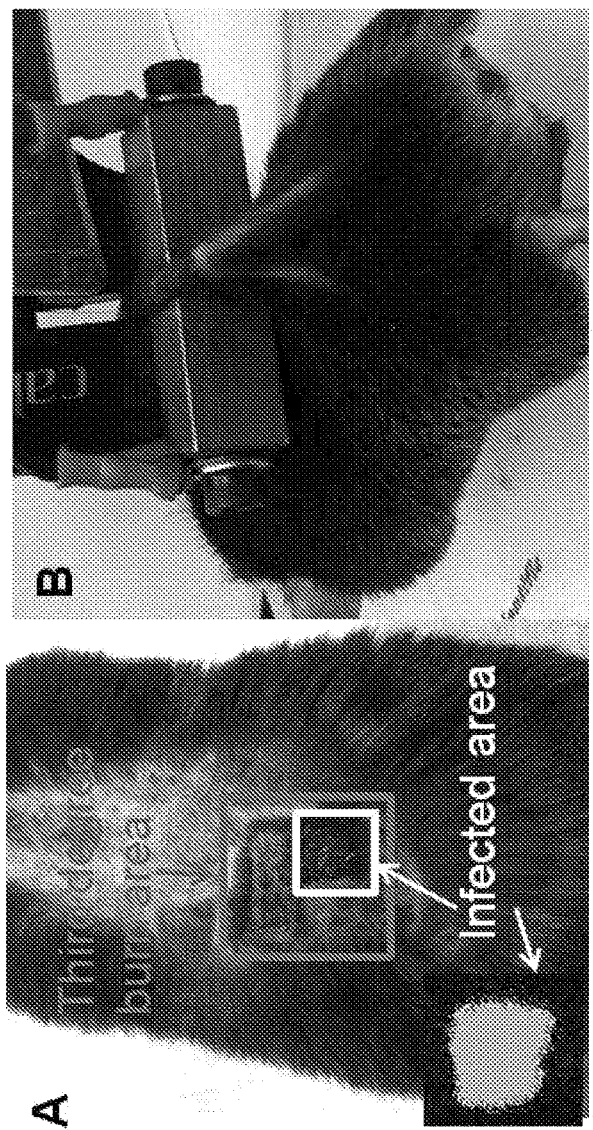
FIG. 21 is a graphical illustration indicating the delivery of pulsed electric field therapy to infected burned mice skin.
Figure 21:
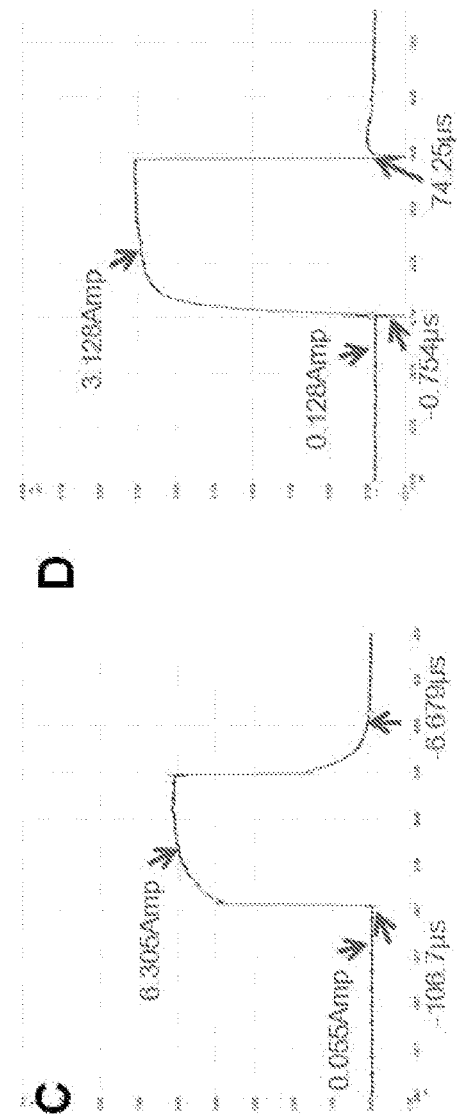

Plate Electrodes Allow for Surface Treatment with Controlled Electrical Pulse Parameters A timeline illustrating the experimental design appears in FIG. 20. At an initial time $T_0$, third degree burns were induced, followed by infection with *A. baumannii* 5 min after the burn, and two treatments with pulsed electric fields consisting of 40 pulses per treatment. Bioluminescent imaging was used throughout the experiment for monitoring infection. The third degree burn created immediate demarcation in the skin (FIG. 21A). The representative bioluminescent signal registered from the infected area is shown in FIG. 21A.

The procedure for pulsed electric field delivery is demonstrated in FIG. 21B. Two plate electrodes were positioned on the infected area for pulse delivery. FIG. 21C shows the representative shape of pulses when 1000 Volts were applied between the electrodes. FIG. 21D shows the representative shape of pulses when 500 Volts were applied between the electrodes. The maximum current at the 1000 Volts treatment was 6.4±0.7 Amp and the maximum current at the 500 Volts treatment was 3.1±0.4 Amp. The measured values were used for the modeling of thermal effects of pulsed electric fields as described in the following sections.

Pulsed Electric Fields Deliver Homogeneous Full Thickness Treatment

To study the electric field distribution within the infected skin as well as the possible thermal effects of pulsed electric fields on the wound, we constructed a 2D numerical model using Finite Elements Methods (FEM). We modeled the geometry of burned mice skin located between plate electrodes for pulsed electric field treatment. The scheme of the model appears in FIG. 22A, and the electric and thermal properties of the skin layers are located in Table I. The electrical conductivity of the burned and infected tissue was calculated using Pouillet's law:

$$\sigma = \frac{IL}{AV} \quad (1)$$

where $\sigma$ is the electrical conductivity (S/m), L (m) is the distance between electrodes, I (Amp) is the measured current, V (Volt) is the applied voltage, and A (m$^2$) is the surface area of the electrodes.

Several assumptions were made in this experiment. First, tissue has considered to have both electrical resistive and capacitive properties, with capacitor charging time negligible in comparison to the pulse length. Second, with tissue membranes assumed destroyed during the burn, and thermal properties of burnt tissue were considered to be the same as that of normal tissue. These allow for the use of DC conductance models in calculating the distribution of the electric fields in the infected tissue.

To calculate the electric fields distribution, we used the Laplace equation:

$$\nabla^2 U = 0 \quad (2)$$

with the boundary conditions that the left electrode (shown in FIG. 22 A) delivers 1000 Volts in simulation 1, or 500 Volts in simulation 2 and right electrode held at 0 Volts.

Figure 22:
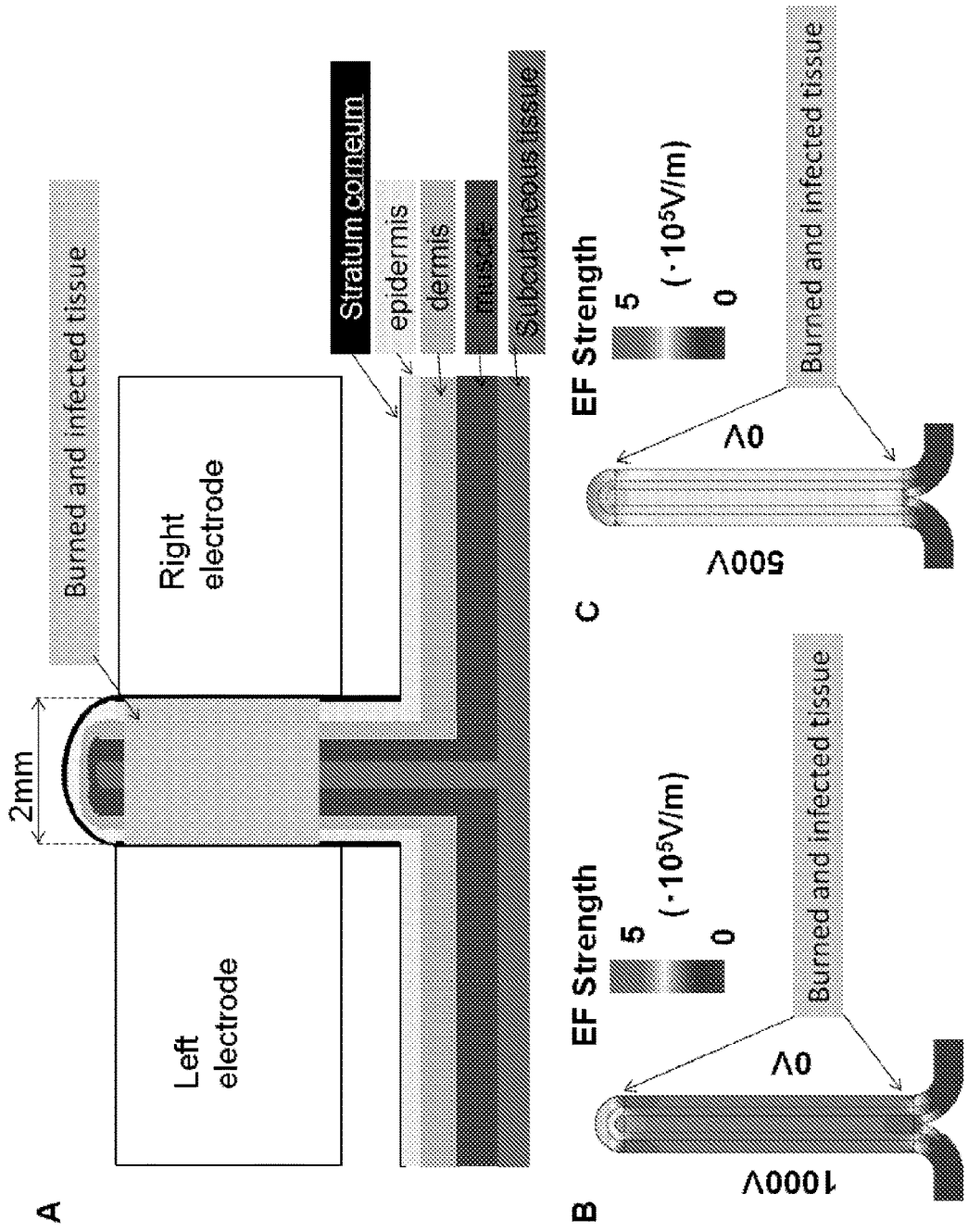
FIG. 22 is a graphical illustration indicating the electric field distribution in infected burned mice skin and adjusted normal skin.

Finite element methods (FEM) are typically used in studying electric field distribution with complex geometry of objects with different electric properties. FIG. 22B and FIG. 22C illustrate map of the electric field distribution in the skin containing a burned/infected area, showing relatively homogeneous distribution of electric fields in the burned areas. Specifically, FIG. 22 B reveals the spatial distribution of electric fields when 1000 Volts were applied through the left electrode. The model extrapolation shows that field strength was homogeneous distributed in the burned area and was about 490 V/mm. FIG. 22C shows the spatial distribution of electric fields in the treated area when 500 Volts were applied through the left electrode. The model analysis shows that the field strength was homogeneous in the treated region around 247 V/mm.

The Effect of Pulsed Electric Fields on Bacteria is Non-Thermal

Simulations were carried out using FEM to model the time dependent temperature distribution in the infected area treated by pulsed electric fields. To calculate the temperature increase resulting from the pulsed electric fields application, we solved for the transient heat transfer value using the following equation:

$$\frac{\partial}{\partial x}\left(\lambda_x \frac{\partial T}{\partial x}\right) + \frac{\partial}{\partial y}\left(\lambda_y \frac{\partial T}{\partial y}\right) = -q - c_p \frac{\partial T}{\partial t} \quad (3)$$

where T is the temperature (K), $\Delta$ (W K$^{-1}$ m$^{-1}$) is the thermal conductivity, $c_p$ (J K$^{-1}$ kg$^{-1}$) is the specific heat capacitance, t (s) is time, and q (T) is the volume power of heat sources. In our problem q (T is the average power supplied to the tissue by pulses electric fields. The following equation described the calculation of power supplied by square pulsed electric fields:

$$Q_{avg} = \frac{V_{RMS}^2}{R} = \frac{V^2 t_p f}{R} \quad (4)$$

where $Q_{avg}$ (W) is the total average power delivered by square pulsed electric fields, R (ohm) is the resistance, $V_{RMS}$ is the root mean square voltage, V (Volt) is the applied voltage, $t_p$ (s) is the duration of the pulse, and f (Hz) is the frequency of pulse wave. Equation 3 is a partial differential equation. To solve it, the following boundary conditions were used, namely $T_{in}$=37° C. and $T_{air}$=25° C., where $T_{in}$ is the initial temperature of the body and $T_{air}$ is the constant temperature of the air. We assumed heat is transferred by convection between the surfaces of the body and electrodes, and the air. The convection coefficient was 5 W K$^{-1}$ m$^{-2}$.

Figure 23:
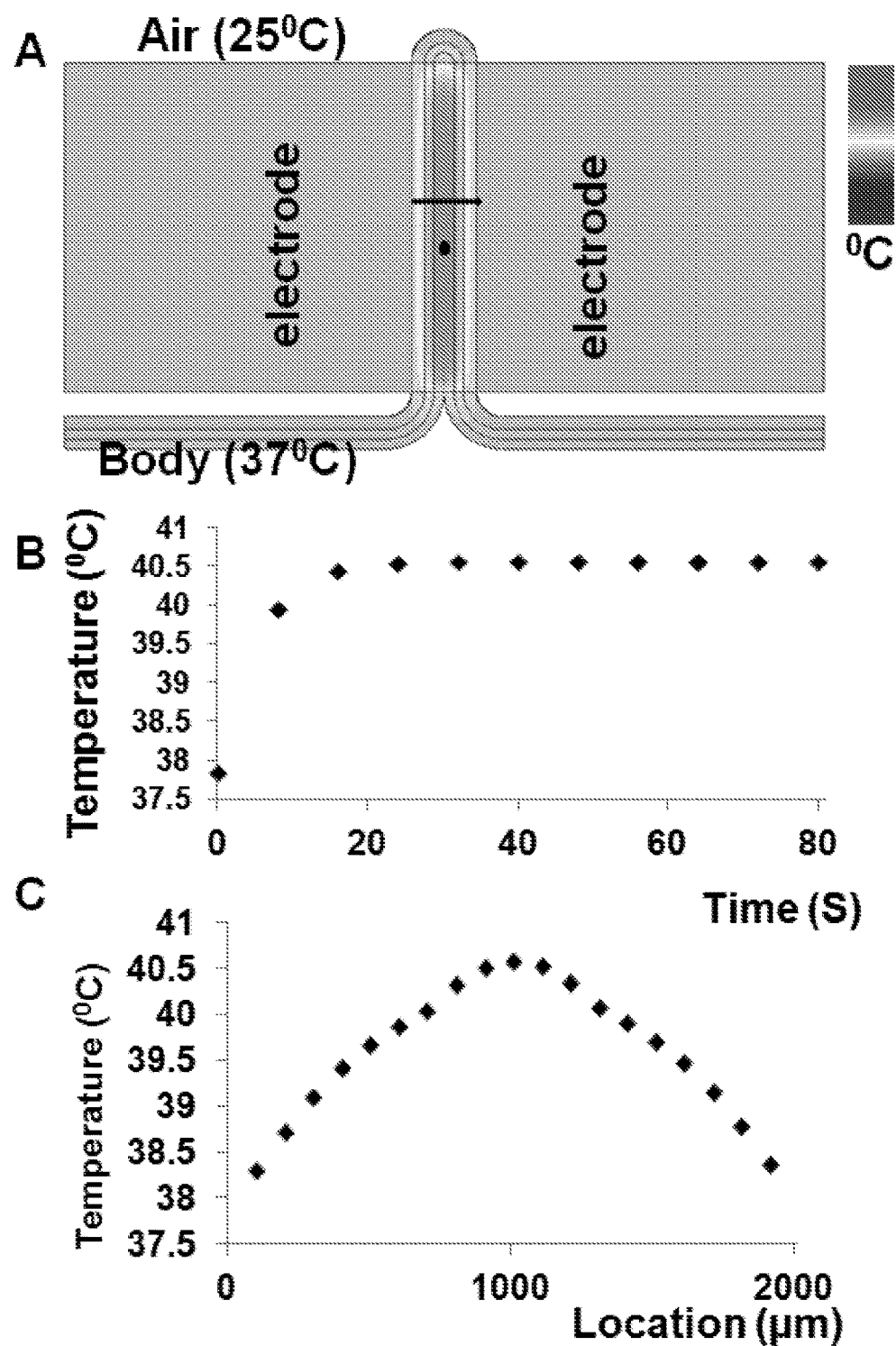
FIG. 23 is a graphical illustration indicating thermal effects of pulsed electric fields delivered to skin.

FIG. 23A shows the solution results for 80 pulses of 1000 Volts applied at 1 Hz. The heated volume is precisely the treated, burned/infected area of the skin. The largest area of heating was in the deep areas of the tissue. FIG. 23B shows the time-depended temperature change in the center of the tissue. It is interesting to note that the temperature increases during first 20 pulses (20 seconds) and then stabilizes in a new steady-state with the surrounding environment. FIG. 23C shows the spatial distribution of temperature in the treated skin after 80 seconds of continuous application of pulsed electric fields. The maximum temperature was observed to be in the center of the treated skin and did not exceed 41° C. Such temperature increase lasting for two minutes is insufficient to cause any thermal damage to bacteria, heat inactivation of which requires higher temperatures of at least 55° C., as well as longer exposure times of greater than 15 minutes. Therefore, our modeling results suggest that all pulsed electric field effects on bacterial load reduction are non-thermal in nature.

Pulsed Electric Fields Reduce Bacteria Load in Burn Wounds

Figure 24:
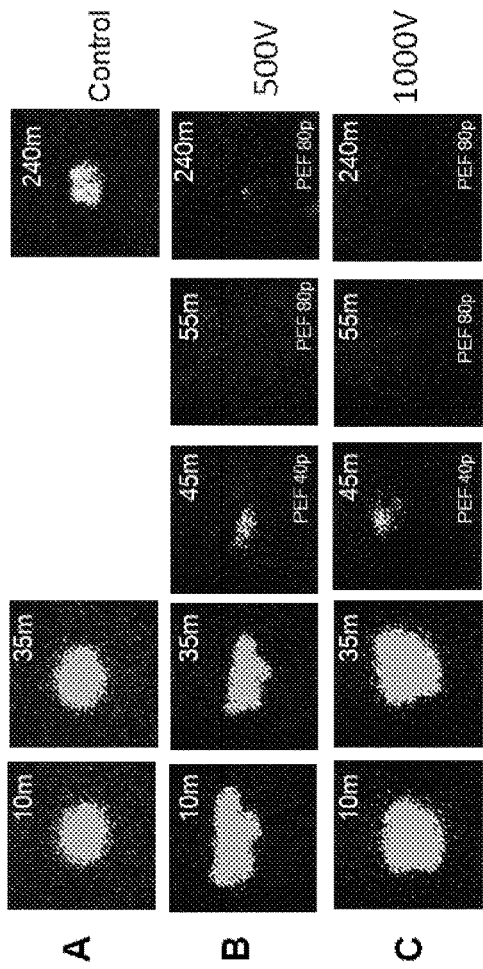
FIG. 24 is a graphical illustration indicating bacterial load reduction by use of pulsed electric fields.
Figure 24:
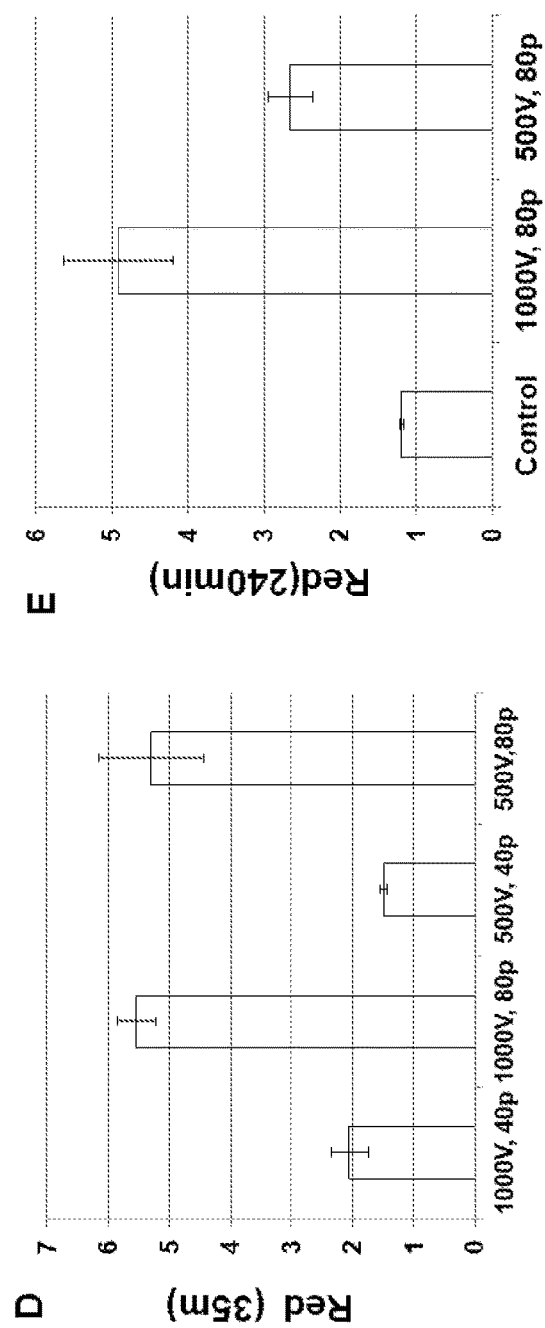

FIG. 24 A-C demonstrate that the bioluminescence signal from the untreated skin, though reduced, is still easily detected using a bioluminescent camera as compared to the treated skin. The bacterial load reduction, as depicted in FIG. 24D, E was calculated using the following equation:

$$\text{Red} = \log_{10} \frac{RLU_{bt}}{RLU_{at}} \quad (5)$$

where $R_{ed}$ is the $\log_{10}$ reduction of bacteria load, $RLU_{bt}$ is the RLU measurement of the infected skin before treatment with PEF, and $RLU_{at}$ is the RLU measurement of the infected skin at various time points after pulsed electric field treatments. The standard deviation of the mean is calculated.

The 1 $\log_{10}$ reduction in the bioluminescence signal measured at the untreated, infected skin (control site, FIG. 24 A) four hours after the burn is most likely secondary to the penetration of bacteria into the deep tissue and natural death of a portion of the bacterial population. FIG. 24 A, B, C show that the population of bacteria on the skin surface during first 30 min after infection did not change, and hence, the infection was stable. However, the application of 40 pulses at 500 Volts reduced the bioluminescence signal, representing a reduction in the bacteria load by 1.49±0.07 Log 10 (FIG. 24D). The bioluminescent signal was further reduced after treatment with 80 pulses at 500 Volts, correlating to a 5.30±0.85 Log 10 reduction in the bacteria load immediately after treatment (FIG. 24D). However, three hours after treatment, the total reduction was only 2.66±0.30 Log 10 (FIG. 24E).

Next, the voltage delivered through the left electrode was increased to 1000 from 500 Volts. A treatment of 40 pulses at 1000 Volts reduced the bioluminescent signal, representing a decrease in bacterial load by 2.04±0.29 Log 10 (FIG. 24D). Completing 80 pulses at 1000V, further reduced the bioluminescent signal and bacterial load by 5.53±0.30 Log 10 immediately after treatment FIG. 24D). Three hours after treatment, the total reduction was 4.91±0.71 Log 10 (FIG. 24E).

Discussion

Pulsed electric fields were efficient in the disinfection of infected burned murine skin. Using 80 pulses of 500 V/mm, we achieved stable disinfection with 4.91±0.71 Log 10 reduction of *Acinobacter baumanii* load, three hours after infection (FIG. 24). Mathematical modeling demonstrate that pulsed electric fields penetrate homogeneously (FIG. 21) through the entire segment of infected tissue and bacterial load reduction was non-thermally (FIG. 22). This is the first report on the treatment of wound bacterial infection with non-thermal pulsed electric fields.

Bacterial re-growth due to recontamination or incomplete disinfection is commonly appreciated after all types of disinfection technologies. It was shown in previous studies that bacterial disinfection by pulsed electric field follows Weibull or Fermi distributions as a function of electric fields strength and pulse number. In this paper we observed bacterial re-growth when using low doses of electric fields (FIG. 24). To address the re-growth problem, pulsed electric fields may be applied intermittently on the targeted area for an indefinite period of time to prevent recontamination. Such application frequency may be defined by the bacterial re-growth rate.

Cells with a large diameter may be more vulnerable to PEF as compared to smaller cells. Therefore, pulsed electric fields destroying bacteria may likely affect the host cells which survived the burn injury. This non-selectivity of the pulsed electric field method may be a concern when treating infection in healthy uninjured tissue. To address the effects of pulsed electric fields on the non-target tissue, we have previously investigated the healing process of normal healthy skin ablated by pulsed electric fields. Our results show that pulsed electric fields are selective to the cell membrane, while preserving the extracellular matrix (ECM) and the vasculature of the treated area. More importantly, we showed that pulsed electric field-ablated skin regenerated without scars.

The disinfection effect was correlated with both the electric field strength and the number of delivered pulses. Specifically, the increase in pulse number was shown to achieve a larger reduction in bacterial load and bioluminescence signal immediately after treatment, as compared to the increase in the field strength. Increasing the pulse number from 40 to 80, led to ~255% increase in the log reduction of bacterial load in the wound. Increasing the applied voltage from 500 V to 1000V while keeping the number of pulses at 40, however, led to ~37% increase in the log reduction of bacterial load in the wound.

The increase in disinfection capability using pulsed electric fields does not correlate with the increase of energy consumption. To calculate the invested energy we used:

$$E = V_{RMS} I_{RMS} T \quad (6)$$

where E (Joule) is the total invested energy in Joules, $I_{RMS}$ (Amp) is the root mean square of the current, and T(s) the total application time. For delivery of 80 pulses with 250 V/m at 1 Hz, ~9 Joules are needed. For delivery of 40 pulses with 500 V/mm at 1 Hz, ~18 Joules are needed. These energy consumption findings are interesting, showing that increasing the number of pulses from 40 to 80, leads to a significantly larger bacterial load reduction than may be achieved by increasing the electric field strength from 250 V/mm to 500 V/mm, therefore requiring less invested energy. These findings are strikingly different from disinfection effects based on heat/radiation, where the bacterial load reduction directly correlates with consumed energy. These findings are consistent with the current electroporation theory, according to which increasing field strength increases total electroporated surface of the cell membrane. Increasing number of pulses, after the electroporation threshold potential is reached, increases the number and size of the aqueous pores of the membranes at the electroporated. The novel aspect findings in this study, however, is the first time in vivo demonstration that decreasing the bacterial load can be achieved by consuming less energy, through the application of multiple pulses.

This study provides results using single strain of bioluminescent bacteria. Burns or other wounds can be contaminated by multiple types of microorganisms, of which resistance to antibacterial therapies may increase in heterogeneous communities. Therefore, future studies on the effects of pulsed electric fields on bacteria in wounds may benefit from evaluating of heterogeneous organism populations.

In conclusion, throughout evolution mammals have lost the ability to regenerate anatomy and function of injured organs in large because of excessive scar formation. Hypertrophic skin scarring leads to major physical, aesthetic, functional, psychological, and social stresses on patients. Recent data show that alterations in coagulation, inflammation, angiogenesis, fibroplasia, contraction, remodeling and mechanical tension correlate with the formation of proliferative scars. Studies also demonstrate that proliferative scar formation may be associated with tissue microenvironment and signaling, which in turn depends on extracellular matrix composition and architecture, local cell-cell interaction, and perfusion-borne inflammation. Challenging questions still remain regarding how to modulate this complex set of phenomena to reduce proliferative scar formation.

Proliferative scarring is a condition with no known molecular mechanism, and no effective treatment is available today for this common and important pathologic condition. Current understanding of fibroblast kinetics suggests that deregulation of fibroblast signaling and delayed apoptosis are involved in pathologic scarring. As such, the present invention recognizes that pulsed electric fields delivered periodically or intermittently may contribute to the treatment of proliferative scarring by providing precise spatial and temporal targeting of specific cells, such as fibroblast cell density. Therefore, systems and methods are provided for non-chemically controlling tissue repair and regenerative processes using pulsed electric fields.

Using controlled pulse strength, duration, frequency, and temporal delivery, systems and methods of the present invention may provide for enhanced outcomes compared to other non-specific, chemical, surgical and ablative approaches, by allowing for selective targeting of specific cell types, agents or bacteria, as well as allow for extended control of cell, agent or bacteria density without significant effect of tissue matrix or tissue mechanical properties.

As described, the benefits from application of electric field pulses were investigated. Specifically, the growth, death, and regeneration of normal human dermal fibroblasts in culture were studied, illustrating that fibroblast survival depends on the number of applied pulses and follows a Weibull distribution. These initial results suggested that pulsed electric fields may prove useful as a non-chemical method for improvement in wound healing, by controlling certain elements in the scar formation process. Further studies on rats showed that skin subjected to injury may regenerate with no signs of fibrosis using pulsed electric fields, providing in vivo demonstrations for control of fibroblast cell density. Such finding is significant in the development of a new method for treating non-healing wounds, hypertrophic scars and keloids. Additionally, results from rat studies also showed increased collagen and ellastin fiber density in skin treated with pulsed electric fields, suggesting advantageous use in the field of basic regenerative medicine, developmental biology research and cosmetic rejuvenation. Moreover, studies involving bacterial infection at burn injury sites further demonstrated use of pulsed electric fields, as described, by illustrating antiseptic capabilities. By using a non-thermal approach for wound disinfection, pulsed electric fields potentially destroy bacteria through the irreversible creation of pores.

The systems and methods of present invention, as described, present clinical significance with basic science implications, and broad impact in regenerative and trauma medicine. As such, important advances in treatment of acute and chronic wounds associated with both non-healing, or infected wounds, as well as hypertrophic scarring can be expected from the present invention, potentially overcoming the problems associated with other surgical or chemical therapies. Such approach may be extended to therapies that could include multiple targets thought to be responsible for undesired effects during tissue repair and development.

Additionally, pulsed electric fields, as described, may significantly increase the effectiveness of currently used antibiotics through synergistic effects, providing alternative approaches for combating infections in clinics. For example, it may be advantageous to combine pulsed electric field technology, as described, with existing antibiotic regimens. In this manner, pulsed electric fields may not only increase drug penetration into bacteria cells, but may also induce increased drug diffusion in biofilms. Among general populations, this combined approach, may advantageously benefit certain patients, such as burn victims.

The various configurations presented above are merely examples and are in no way meant to limit the scope of this disclosure. Variations of the configurations described herein will be apparent to persons of ordinary skill in the art, such variations being within the intended scope of the present application. In particular, features from one or more of the above-described configurations may be selected to create alternative configurations comprised of a sub-combination of features that may not be explicitly described above. In addition, features from one or more of the above-described configurations may be selected and combined to create alternative configurations comprised of a combination of features which may not be explicitly described above. Features suitable for such combinations and sub-combinations would be readily apparent to persons skilled in the art upon review of the present application as a whole. The subject matter described herein and in the recited claims intends to cover and embrace all suitable changes in technology.

The invention claimed is:

1. A method for treating a tissue of a subject using pulsed electric fields, the method comprising:
engaging an electrode assembly of a treatment system with a non-wounded skin tissue of a subject;
receiving an instruction for delivering a pulsed electric field to the skin tissue;
generating, using the instruction, a non-thermal ablative pulsed electric field, the pulsed electric field defined by electric field parameters including a pulse duration, a pulse frequency, a pulse number, and a pulse amplitude; and
directing the electrode assembly to deliver the pulsed electric field using the electric field parameters to increase at least one of collagen and elastin fiber density in at least a portion of the skin tissue without causing scarring.

2. The method of claim 1, wherein generating the electric field parameters includes selecting:
70 microseconds for the pulse duration,
2 Hertz for the pulse frequency,
180 pulses for the pulse number, and
250 Volts per millimeter for the pulse amplitude.

3. The method of claim 2, wherein generating the electric field parameters includes selecting four pulse series of 45 pulses for the pulse number and a time period between pulse series.

4. The method of claim 3, wherein the time period between pulse series is thirty seconds.

5. The method of claim 1, further comprising generating the electric field parameters in a combination configured to produce non-thermal effects to the skin tissue, wherein the non-thermal effects are described by temperature changes of up to 40 degrees Celsius.

6. The method of claim 1, wherein generating the electric field parameters includes selecting at least one of:
a range between 100 nanoseconds and 100 milliseconds for the pulse duration,
a range between 0.1 and 5000 Hertz for the pulse frequency,
a range between 1 and 5000 pulses for the pulse number, and
a range between 1 and 5000 Volts for the pulse amplitude.

7. The method of claim 1 and further comprising delivering the pulsed electric field, based on the electric field parameters, to the skin tissue a plurality of times with pauses between each delivery.

* * * * *

UNITED STATES PATENT AND TRADEMARK OFFICE
CERTIFICATE OF CORRECTION

PATENT NO. : 10,183,163 B2  
APPLICATION NO. : 14/655178  
DATED : January 22, 2019  
INVENTOR(S) : Alexander Golberg et al.

Page 1 of 1

It is certified that error appears in the above-identified patent and that said Letters Patent is hereby corrected as shown below:

In the Specification

Column 21, Line 33, "Δ" should be --$\lambda$--.

Signed and Sealed this
Nineteenth Day of March, 2019

Andrei Iancu
*Director of the United States Patent and Trademark Office*